US011444049B2

(12) United States Patent
Maki

(10) Patent No.: US 11,444,049 B2
(45) Date of Patent: Sep. 13, 2022

(54) ELECTRONIC COMPONENT MODULE, METHOD FOR PRODUCING THE SAME, ENDOSCOPIC APPARATUS, AND MOBILE CAMERA

(71) Applicant: SONY CORPORATION, Tokyo (JP)

(72) Inventor: Osamu Maki, Aichi (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/637,521

(22) PCT Filed: Aug. 7, 2018

(86) PCT No.: PCT/JP2018/029596
§ 371 (c)(1),
(2) Date: Feb. 7, 2020

(87) PCT Pub. No.: WO2019/035392
PCT Pub. Date: Feb. 21, 2019

(65) Prior Publication Data
US 2020/0219836 A1 Jul. 9, 2020

(30) Foreign Application Priority Data
Aug. 14, 2017 (JP) .............................. JP2017-156371

(51) Int. Cl.
*H01L 23/00* (2006.01)
*G02B 23/24* (2006.01)
*H01L 23/498* (2006.01)
*H01L 27/146* (2006.01)

(52) U.S. Cl.
CPC .......... *H01L 24/16* (2013.01); *G02B 23/2484* (2013.01); *H01L 23/49811* (2013.01);
(Continued)

(58) Field of Classification Search
CPC ............... H01L 24/16; H01L 27/14636; H01L 23/49838; H01L 23/49811; H01L 23/32484; G02B 23/2484
See application file for complete search history.

(56) References Cited

U.S. PATENT DOCUMENTS 10,299,376 B2 * 5/2019 Nakamura ............... H01B 1/22
2005/0106902 A1 5/2005 Hougham et al.
(Continued)

FOREIGN PATENT DOCUMENTS

JP 2004-087694 3/2004
JP 2005-150750 6/2005
(Continued)

OTHER PUBLICATIONS

International Search Report prepared by the Japan Patent Office dated Sep. 26, 2018, for International Application No. PCT/JP2018/029596.

*Primary Examiner* — Caridad Everhart
(74) *Attorney, Agent, or Firm* — Sheridan Ross P C.

(57) ABSTRACT

An electronic component module according to an embodiment includes a substrate, an electronic component, and a connection device. The substrate includes an electrode array. The electronic component includes an electrode array. The connection device that includes a plurality of post parts including respective conductive parts and a base for supporting the plurality of post parts. The connection device is interposed between the substrate and the electronic component, and is configured in a manner that the conductive parts electrically connect the electrode array of the substrate and the electrode array of the electronic component to each other via solder.

20 Claims, 24 Drawing Sheets

(52) U.S. Cl.
CPC ........ *H01L 23/49838* (2013.01); *H01L 24/11* (2013.01); *H01L 24/81* (2013.01); *H01L 27/14636* (2013.01); *H01L 27/14683* (2013.01); *H01L 2224/1111* (2013.01); *H01L 2224/1146* (2013.01); *H01L 2224/11464* (2013.01); *H01L 2224/11612* (2013.01); *H01L 2224/11614* (2013.01); *H01L 2224/16058* (2013.01); *H01L 2224/16227* (2013.01); *H01L 2224/81801* (2013.01)

(56) References Cited

U.S. PATENT DOCUMENTS

| | | |
|---|---|---|
| 2009/0321122 A1 | 12/2009 | Mori et al. |
| 2011/0020588 A1* | 1/2011 | Shimizu ............ F04B 43/0736 428/80 |
| 2014/0240566 A1* | 8/2014 | Shizukuishi ...... H01L 27/14634 348/302 |
| 2015/0380377 A1* | 12/2015 | Uzoh .................... H01L 23/42 257/773 |
| 2016/0309585 A1 | 10/2016 | Nakamura |

FOREIGN PATENT DOCUMENTS

| | | |
|---|---|---|
| JP | 2005-216696 | 8/2005 |
| JP | 2010003854 A | 1/2010 |
| JP | 2011-042818 | 3/2011 |
| TW | 201503771 A | 1/2015 |
| TW | 201640973 A | 11/2016 |
| WO | WO 2007/116657 | 10/2007 |

\* cited by examiner

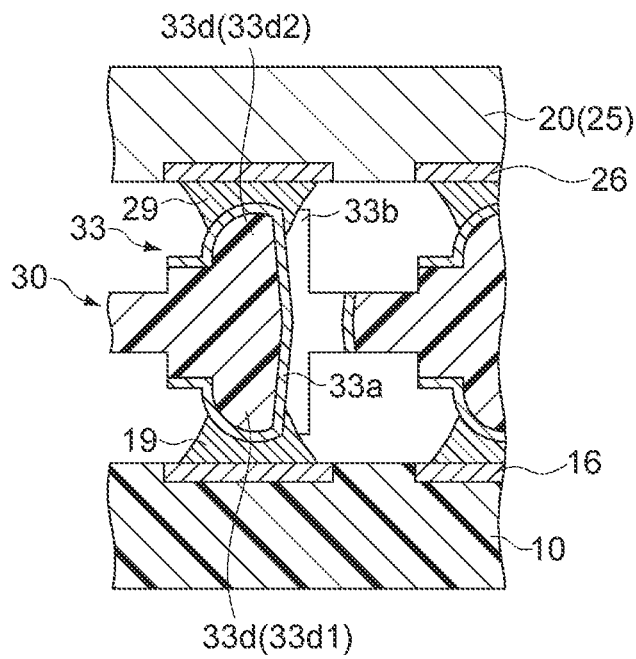
FIG.4
| | | Number of damaged terminals | Number of samples including completely broken terminals |
|---|---|---|---|
| Module including MID | Component side | 105 terminals / 1280 terminals | 4 samples / 10 samples |
| | Substrate side | None / 1280 terminals | None / 10 samples |
FIG.5
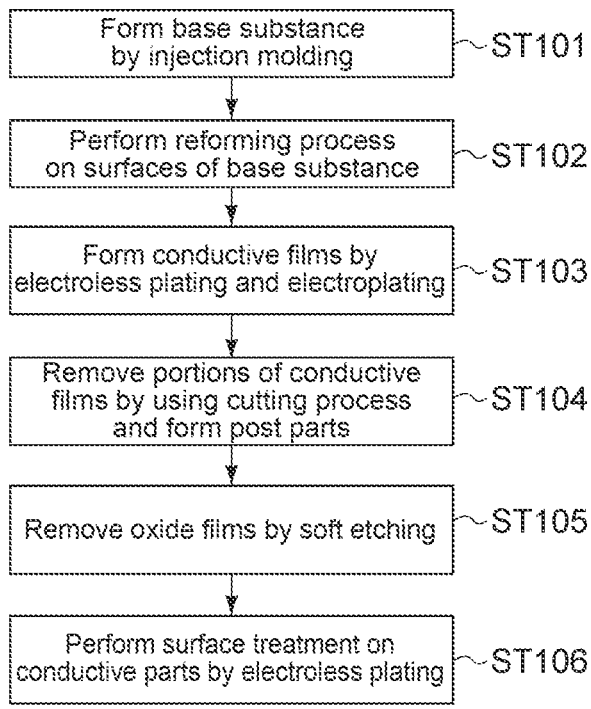
FIG.6

ELECTRONIC COMPONENT MODULE, METHOD FOR PRODUCING THE SAME, ENDOSCOPIC APPARATUS, AND MOBILE CAMERA

CROSS REFERENCE TO RELATED APPLICATIONS

This application is a national stage application under 35 U.S.C. 371 and claims the benefit of PCT Application No. PCT/JP2018/029596 having an international filing date of 7 Aug. 2018, which designated the United States, which PCT application claimed the benefit of Japanese Patent Application No. 2017-156371 filed 14 Aug. 2017, the entire disclosures of each of which are incorporated herein by reference.

TECHNICAL FIELD

The present technology relates to a technology of an electronic component module that mainly includes an image pickup element as an electronic component.

BACKGROUND ART

According to a method for producing a three-dimensional molded interconnect device described in Patent Literature 1, a catalyst is applied to a surface of an insulation base substance, and a portion of the catalyst is removed through laser irradiation. Subsequently, a predetermined region on the insulation base substance is covered with mask material and is subjected to electroless plating, and this makes it possible to form a circuit on a portion with the residual catalyst (for example, see FIG. 1 and paragraphs [0025] to [0027] in the specification of Patent Literature 1).

CITATION LIST

Patent Literature

Patent Literature 1: JP 2011-42818A

DISCLOSURE OF INVENTION

Technical Problem

Meanwhile, the following problems arise in the case where an electronic component module is formed by soldering an electronic component and a substrate on which the electronic component is to be mounted and the electronic component module is used in a temperature cycling environment. For example, in the case where main material of the electronic component is different from main material of the substrate, thermal stress and thermal strain may occur due to difference in coefficients of thermal expansion between the main material of the electronic component and the main material of the substrate, and solder that connects them may crack.

A purpose of the present disclosure is to provide an electronic component module and a method for producing the same, the electronic component module making it possible to alleviate the thermal stress and the thermal strain that occur due to difference in coefficients of thermal expansion between a substrate and an electronic component. In addition, a purpose of the present disclosure is to provide an endoscopic apparatus and a mobile camera that use the electronic component module.

Solution to Problem

To achieve the above-described purpose, an electronic component module according to an embodiment includes a substrate, an electronic component, and a connection device.

The substrate includes an electrode array.

The electronic component includes an electrode array.

The connection device that includes a plurality of post parts including respective conductive parts and a base for supporting the plurality of post parts. The connection device is interposed between the substrate and the electronic component, and is configured in a manner that the conductive parts electrically connect the electrode array of the substrate and the electrode array of the electronic component to each other via solder.

The post parts standing on the base of the connection device interposed between the substrate and the electronic component make it possible to absorb and alleviate thermal stress and thermal strain that occur due to difference in coefficients of thermal expansion between the substrate and the electronic component.

The connection device may have a plurality of through holes in which the respective conductive parts are disposed. This makes it possible to achieve a structure of electrically connecting the substrate to the electronic component.

Axis centers of the through holes may be disposed in a manner that the axis centers of the respective through holes are deviated from axis centers of the post parts.

Axis centers of the respective through holes may coincide with axis centers of the post parts.

The base may have a first surface that faces the substrate and a second surface that faces the electronic component, and the post parts may include main bodies that protrude from at least one of the first surface or the second surface.

Height of the main bodies from the first surface may be different from height of the main bodies from the second surface.

It is possible for a designer to appropriately design the height of the post parts in accordance with difference in coefficients of thermal expansion between the substrate and the connection device and difference in coefficients of thermal expansion between the electronic component and the connection device.

At least one of the post parts may include a step part that is formed like a step from the base.

In the case of forming the post parts or adjusting the height of the post parts through cutting, it is possible to easily form the post parts with a desired rigidity by forming some or all of the post parts like a step from the base.

Main material of the connection device may be resin.

A Young's modulus of the resin is smaller than Young's moduli of respective main materials of the substrate and the electronic component. Therefore, the connection device makes it possible to effectively absorb thermal stress and thermal strain.

A Young's modulus of the main material of the connection device may be smaller than a Young's modulus of the solder.

An endoscope according to an embodiment includes the image sensor module.

A mobile camera according to an embodiment includes the image sensor module.

A method for producing an electronic component module according to an embodiment includes forming a connection device that includes a plurality of post parts including respective conductive parts and a base for supporting the plurality of post parts.

The electrode array of the substrate and the electrode array of the electronic component are electrically connected to each other via solder by using the conductive parts of the connection device.

The formation of the connection device may include forming a conductive film on a base substance, and forming the conductive parts and the post parts including the conductive parts by removing a portion of the conductive film through cutting of the base substance on which the conductive film is formed.

Formation of the connection device may include forming the base and main bodies of the post parts through injection molding in a manner that the main bodies protrude from a surface of the base, and forming the respective conductive parts on the formed main bodies.

This makes it possible to omit a production process in comparison with the above-described case of forming the main bodies of the post parts through cutting.

Advantageous Effects of Invention

As described above, according to the present technology, it is possible to alleviate the thermal stress and the thermal strain that occur due to difference in coefficients of thermal expansion between the substrate and the electronic component.

Note that the effects described here are not necessarily limited, and any effect that is described in the present disclosure may be exhibited.

BRIEF DESCRIPTION OF DRAWINGS

FIG. 4 is a cross-sectional view of a portion of an image sensor module configured in a manner that an MID is interposed between a substrate and an image sensor that are connected via solder.

FIG. 5 is a table showing results of thermal shock testing with regard to samples of modules including MIDs.

FIG. 6 is a flowchart illustrating a method for producing an MID according to a first example.

MODE(S) FOR CARRYING OUT THE INVENTION

Hereinafter, embodiments of the present technology will be described with reference to the drawings.

1. First Embodiment 1.1) Configuration of Electronic Component Module

Figure 1:
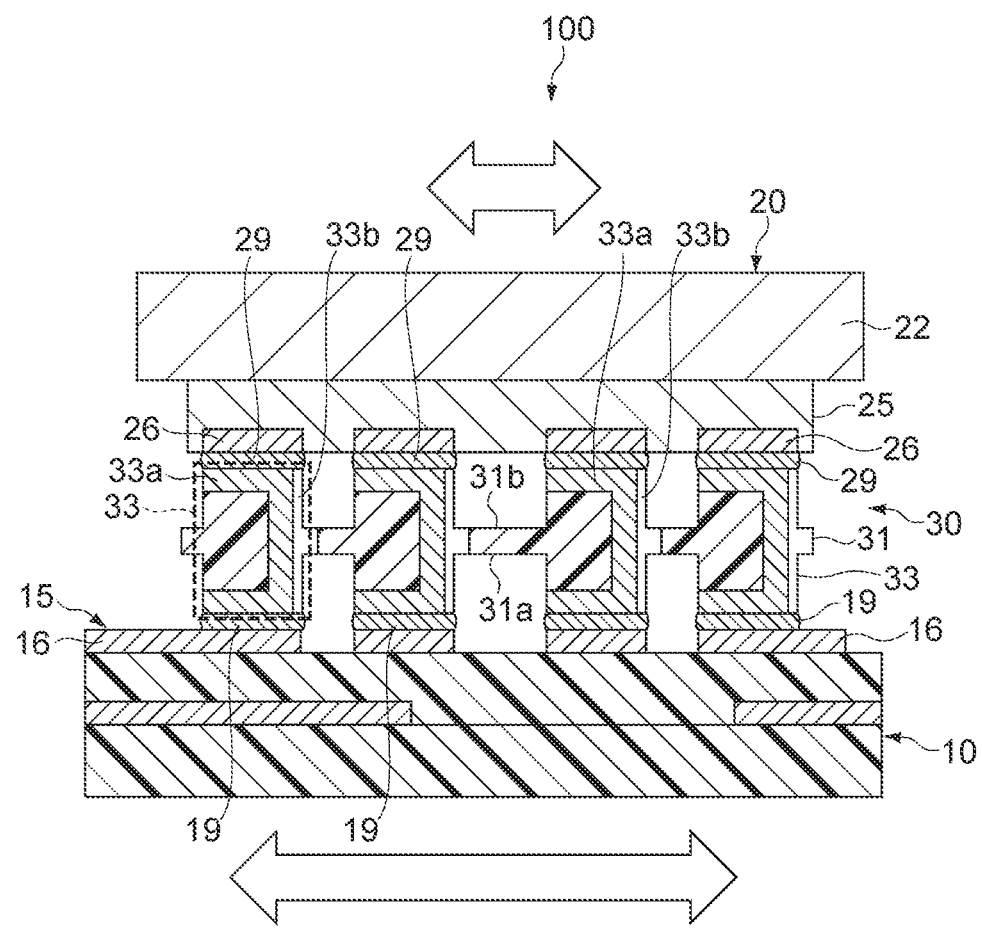
FIG. 1 is a schematic cross-sectional view of an image sensor module that serves as an electronic component module according to a first embodiment.

FIG. 1 is a schematic cross-sectional view of an image sensor module that serves as an electronic component module according to a first embodiment. An image sensor module 100 includes a substrate 10, an image sensor 20 that serves as an electronic component, and a molded interconnect device (MID) 30 that serves as a connection device interposed therebetween. The MID 30 is a device that electrically and mechanically connects the substrate 10 to the image sensor 20. In other words, the image sensor 20 is disposed above the substrate 10 via the MID 30.

The substrate 10 is a mounting board such as a printed circuit board, and includes an electrode array 15. The electrode array 15 includes a plurality of electrode pads 16.

The image sensor 20 includes a main body 22 and an electrode array unit 25 disposed on a bottom surface of the main body 22. The electrode array unit 25 includes a plurality of electrode terminals 26. The arrangement and the number of the electrode terminals 26 correspond to those of the electrode array 15 of the substrate 10. Typically, the electrode array unit 25 has a ball grid array (BGA) design or a land grid array (LGA) design.

The MID 30 includes a plurality of post parts 33 including respective conductive parts 33a and a base 31 for supporting the plurality of post parts 33. One of the post parts 33 is boxed by a dotted line. The schematic shapes of the post parts 33 are a column shape or a prism shape.

For example, each of the conductive parts 33a includes respective edge parts provided on two ends of one of the post parts 33 that face each other, and a relay part that connects the ends. The relay part is disposed in a through hole 33b made along a length direction (a vertical direction in FIG. 1) of the post parts 33. The edge parts provided on the substrate 10 side of the conductive parts 33a are connected to the respective electrode pads 16 of the substrate 10 via solder 19. The edge parts provided on the image sensor 20 side of the conductive parts 33a are connected to the respective electrode terminals 26 of the image sensor 20 via solder 29.

Base material (main material) of the electrode array unit 25 of the image sensor 20 is a ceramic. Base material (main material) of the substrate 10 is resin such as polyimide or epoxy, for example. Therefore, there is a great difference in coefficients of thermal expansion (for example, linear expansion coefficients) between the image sensor 20 and the substrate 10. During usage of the image sensor module 100 over hours or years, it is possible for the MID 30 to absorb and alleviate the difference in coefficients of thermal expansion even in a temperature cycling environment in which heating and cooling are repeated over and over.

Specifically, the MID 30 includes the post parts 33, and it is possible to absorb difference in coefficients of thermal expansion when the post parts 33 are mainly displaced three-dimensionally. Main material of the MID 30 is desirably material having a lower Young's modulus than the Young's modulus of the solder, such as resin. This makes it possible to effectively alleviate the difference in coefficients of thermal expansion between the image sensor 20 and the substrate 10. For example, desirable resin material of the MID 30 is resin with high thermal resistance such as nylon, PEEK, or LCP. Note that, the solder has different melting points depending on its constituent material, but the melting points range roughly from 130° C. to 220° C.

1.2) Specific Examples of MID

Figure 2:
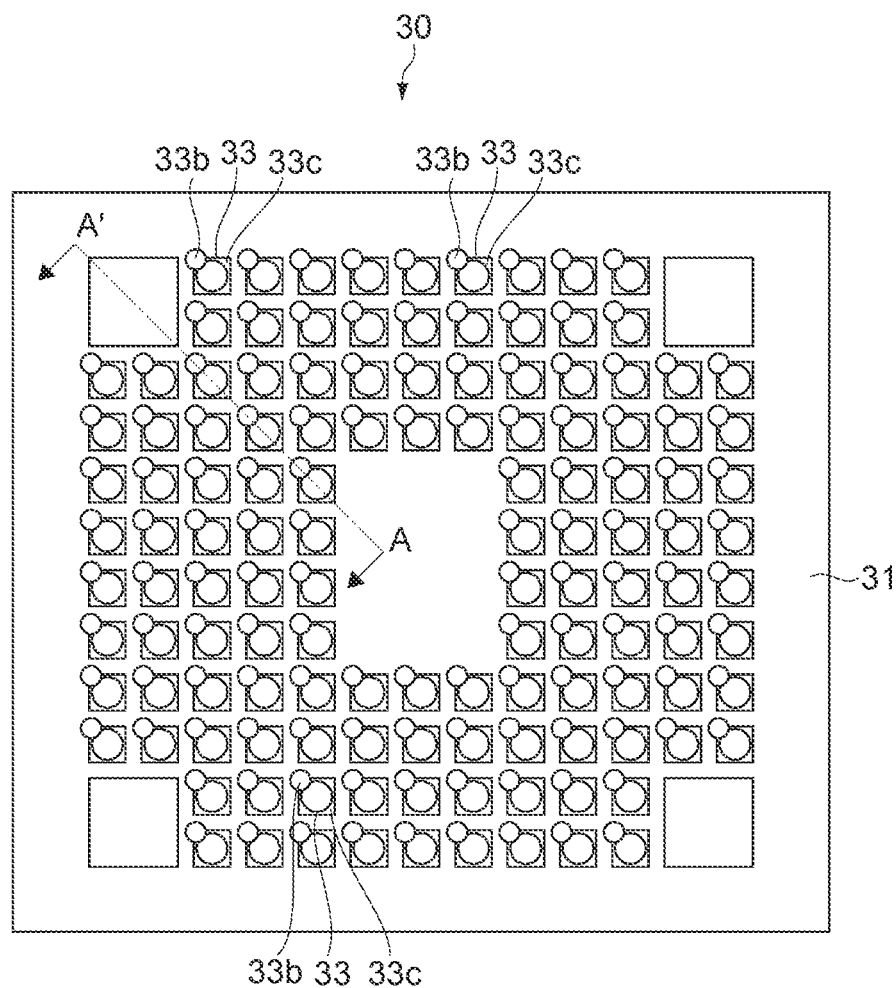
FIG. 2 is a plan view of an MID according to a specific example of the first embodiment.
Figure 3A:
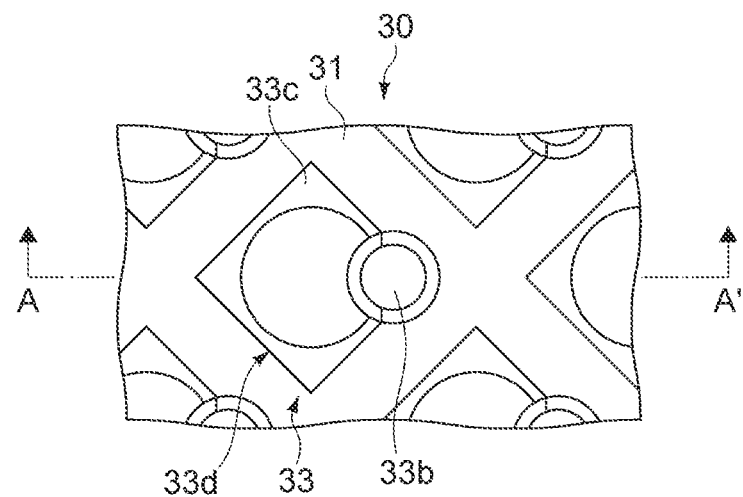
FIG. 3A is an enlarged plan view of the MID.
Figure 3B:
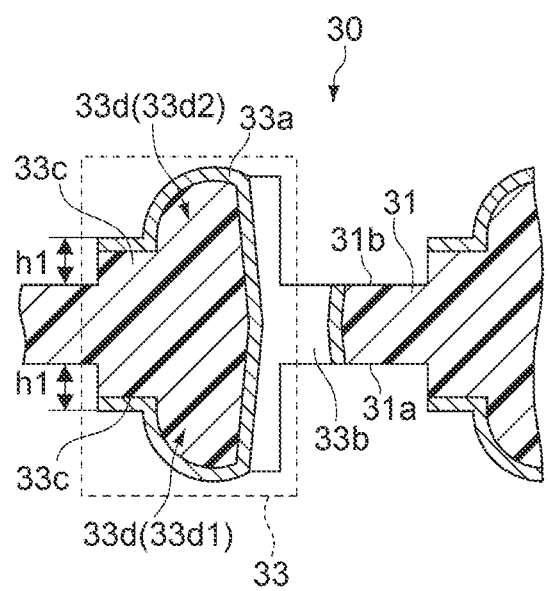
FIG. 3B is a cross-sectional view of the MID taken along a line A-A' of FIG. 3A.

FIG. 2 is a plan view of the MID 30 according to a specific example of the first embodiment. FIG. 3A is an enlarged plan view of the MID 30, and FIG. 3B is a cross-sectional view of the MID 30 taken along a line A-A' of FIG. 3A.

Arrangement of the post parts 33 corresponds to the electrode pads 16 of the substrate 10 and the electrode terminals 26 of the image sensor 20. As illustrated in FIG. 2, the post parts 33 are typically arranged in a matrix in a planar view.

The post part 33 is vertically symmetrical around the base 31. Surfaces of the base 31 include a first surface 31a that faces the substrate 10 and a second surface 31b that is on an opposite side to the first surface 31a and that faces the image sensor 20. Each of the post parts 33 includes a substrate-side protrusion part 33d1 that is a portion of a main body protruding from the first surface 31a toward the substrate 10, and a component-side protrusion part 33d2 that is a portion of a main body protruding from the second surface 31b toward the image sensor 20. Each of the substrate-side protrusion part 33d1 and the component-side protrusion part 33d2 includes a step part 33c that is formed like a step. Note that, when there is no need to discriminate between the substrate-side protrusion part 33d1 and the component-side protrusion part 33d2, they are referred to as "protrusion parts 33d" hereinafter.

A region of the step part 33c has a rectangular shape in a planar view as illustrated in FIG. 2. However, the region is not limited to the rectangular shape, and the region may have a circular shape or another shape. As illustrated in FIG. 3A and FIG. 3B, a through hole 33b is made at one of the four corners of the rectangle in a manner that portions of the protrusion parts 33d are notched. The through hole 33b is made in a manner that the through hole 33b protrudes from the rectangular region of the step parts 33c toward the outside and also penetrates the base 31. In other words, the through hole 33b includes a base penetration region that penetrates the base 31 and a post-part penetration region that penetrates the post part 33. That is, the through hole 33b is disposed in a manner that an axis center of the through hole 33b is deviated from an axis center of the post part 33.

The conductive parts 33a are formed in a manner that the conductive parts 33a serve as conductive films and cover the protrusion parts 33d. As described later, the conductive films cover a molded product in which protrusions other than the step parts 33c are formed through injection molding among the protrusion parts 33d. Next, the protrusion parts 33d including the step parts 33c are formed by cutting the molded product. This makes it possible to isolate the conductive films for the respective post parts 33, and form the conductive parts 33a of the respective post parts 33.

The step part 33c on the first surface 31a side and the step part 33c on the second surface 31b side have the same height h1.

As described later, the step parts 33c make it possible to adjust rigidities of the post parts 33 by appropriately adjusting the sizes, heights, and the like of the step parts 33c.

The conductive parts 33a is formed in the through holes 33b in a manner that the spaces in the through holes 33b are not completely filled with the conductive parts 33a but the conductive parts 33a cover the inner peripheries of the through holes 33b. However, it is also possible to provide the conductive parts in a manner that the through holes 33b are filled with the conductive parts.

FIG. 4 is a cross-sectional view of a portion of the image sensor module 100 configured in a manner that the MID 30 configured as described above is interposed between the substrate 10 and the image sensor 20 that are connected via the solder 19 and the solder 29. The solder 19 is applied to vicinities of the bottom ends of the post parts 33, and the solder 29 is applied to vicinities of the top ends of the post parts 33. The conductive parts 33a of the respective post parts 33 electrically connect the substrate 10 and the image sensor 20 to each other via the solder 19 and the solder 29.

1.3) Thermal Shock Testing

The present inventor conducted thermal shock testing on the module including the MID 30 according to this embodiment. The electrode array unit 25 (of the LGA design here) that does not include the main body 22 of the image sensor 20 but includes a ceramic as base material is only used as an electronic component, and a structure obtained by mounting the electronic component on the substrate 10 via the MID 30 is used as a sample of the module including the MID 30.

FIG. 5 is a table showing results of the thermal shock testing. The present inventor prepared 10 module samples for this thermal shock testing. Next, the modules were input into a thermal shock testing apparatus, thermal shock of repeatedly switching between 0° C. and 130° C. or more was applied 500 times, and damage conditions of the respective soldered parts were observed.

The number of electrode terminals 16 (the number of soldered parts 19) on the component side of each module is 128 (1280 for 10 modules). In the same way, the number of electrode terminals 26 (the number of soldered parts 29) on the substrate 10 side of each module is 128 (1280 for 10 modules).

A result of the testing shows that the number of damaged terminals was 105 in comparison with the total number of terminals. In addition, the number of samples including completely broken terminals was four. According to the above-described results, improvement in yield can be expected.

1.4.) Effects

As described above, according to this embodiment, the post parts 33 supported by the base 31 of the MID 30 interposed between the substrate 10 and the image sensor 20 make it possible to absorb and alleviate thermal stress and thermal strain that occur due to difference in coefficients of thermal expansion between the substrate 10 and the image sensor 20. This makes it possible to suppress cracks in the solder. Therefore, it is possible to improve the yield, and it is possible to obtain the image sensor module 100 with high and long-lasting reliability.

In addition, the MID 30 according to the present technology alleviates not only the thermal shock but also stress that occurs in soldered parts when drop impact or vibration is applied.

1.5.) Production Method

Next, a method for producing the MID 30 will be described. In this specification, seven production methods (a first example to a seven example) will be described.

1.5.1) First Example

Figure 7A:
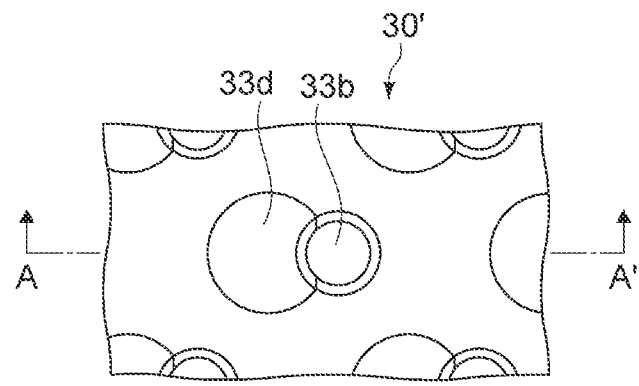
FIG. 7A and FIG. 7B illustrate main parts of an MID under formation by the production method according to the first example.
Figure 7B:
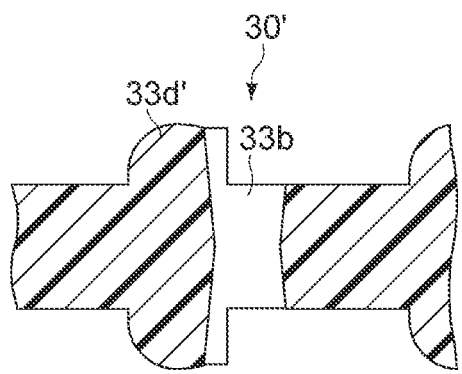
Figure 8:
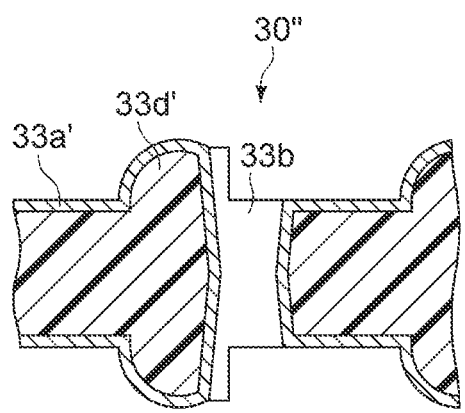
FIG. 8 illustrates main parts of an MID under formation by the production method according to the first example.
Figure 9A:
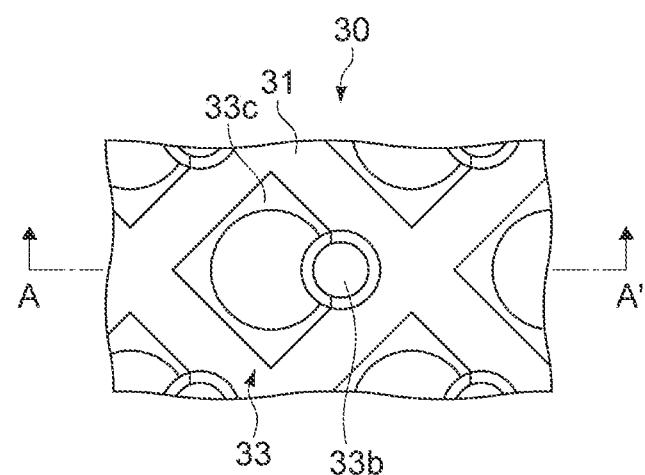
FIG. 9A and FIG. 9B illustrate main parts of an MID formed by the production method according to the first example.
Figure 9B:
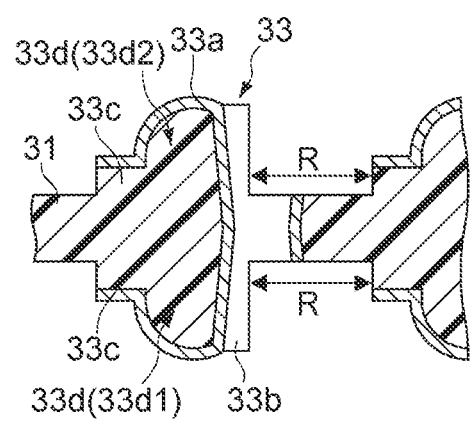

FIG. 6 is a flowchart illustrating a method for producing an MID according to a first example. FIG. 7 to FIG. 9 are diagrams that sequentially illustrate enlarged main parts of an MID 30 with regard to production processes in the production method. FIG. 7A and FIG. 9A are plan views of the MID 30, and FIG. 7B and FIG. 9B are cross-sectional views thereof.

Thermoplastic insulation resin is formed by injection molding (Step (hereinafter, referred to as ST) 101). This makes it possible to form a base substance 30' in which protrusions 33d' and through holes 33b are formed as illustrated in FIG. 7.

A reforming process is performed on the surfaces of the base substance 30' (ST 102). In the surface reforming process, the surfaces are roughened and hydrophilized.

A catalyst of electroless plating is applied to the reformed surfaces of the base substance 30', the electroless plating is performed, and then electroplating is performed (ST 103). This makes it possible to form a base substance 30" with conductive films 33a' formed on the surfaces of the base substance 30' and in the through hole 33b as illustrated in FIG. 8.

As illustrated in FIG. 9A and FIG. 9B, regions R are cut from the base substance 30" on which the conductive films 33a' are formed. This makes it possible to remove portions of the conductive films 33a', form the conductive part 33a (an electrode), and form the post part 33 including the conductive part 33a and the step parts 33c (ST 104). As described above, it is possible to adjust the heights of the post parts 33 and adjust rigidities of the post parts 33 by adjusting the depths (heights) of the step parts 33c to the base 31, that is, the cutting depths of the step parts 33c. In other words, in a design phase, it is possible for a designer of the image sensor module 100 to design the heights of the post parts 33 in accordance with difference in coefficients of thermal expansion between the substrate 10 and the MID 30 and difference in coefficients of thermal expansion between the image sensor 20 and the MID 30.

Meanwhile, in the case of forming the post parts 33 without forming the step parts 33c during the cutting process, sometimes an aspect ratio of the post parts 33 gets too high, and sometimes a desired rigidity may not be obtained. In other words, it is possible to easily form the post parts 33 having an efficient shape and the desired rigidity by forming some or all of the protrusion parts 33d like steps from the base 31.

However, it is also possible to form post parts that does not include the step parts 33c but has a high aspect ratio if a certain type of material is used for the base substance.

Next, an oxide film is removed by soft etching (ST 105). In this embodiment, the cutting process is performed after the conductive film 33a' is formed. Sometimes the oxide film may be formed on the surfaces of the conductive films 33a' because a certain amount of time elapses during the cutting process. Therefore, it is desirable to remove the oxide film before proceeding to a subsequent process.

Next, surface treatment is performed on the conductive parts 33a by electroless plating (ST 106). In ST 106, Ni and Au are formed on surfaces of the conductive parts 33a in this order, for example.

1.5.2) Second Example

Figure 10:
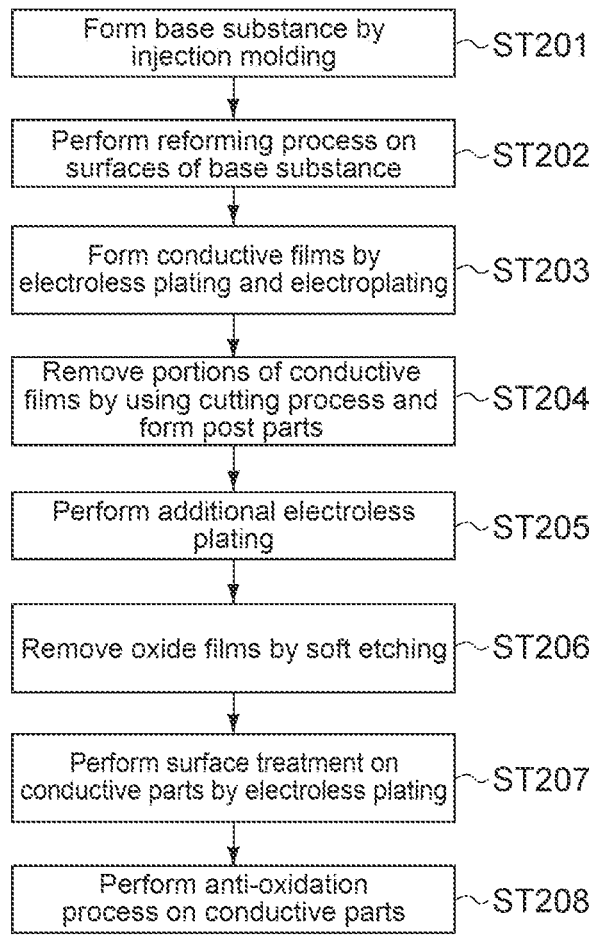
FIG. 10 is a flowchart illustrating a method for producing an MID according to a second example.

FIG. 10 is a flowchart illustrating a method for producing an MID according to a second example. Hereinafter, description will be omitted with regard to steps similar to the production method according to the first example described above, and steps different from the first example will be mainly described. Description thereof will be provided by using reference signs used in FIG. 9A and FIG. 9B.

ST 201 and ST 202 are the same processes as ST 101 and ST 102, respectively. Conductive films 33a' formed in ST 203 are thinner than the case of ST 103. For example, although the film thickness of the conductive films formed in ST 103 is approximately 20 μm, the film thickness of the conductive films formed in ST 203 is approximately 5 μm. This makes it easier to perform a cutting process in ST 204.

In ST 205, preprocessing is performed in a manner that a catalyst is applied in a regionally selective way to a base substance on which post parts 33 including conductive parts 33a are formed, and then additional electroless plating is performed on the conductive parts 33a. Here, the additional electroless plating of approximately 15 μm makes it possible to ensure the film thickness of a whole conductive layer.

ST 206 and ST 207 are the same processes as ST 105 and ST 106, respectively.

In ST 208, an anti-oxidation process is performed on the conductive parts 33*a*. In the anti-oxidation process, an anti-oxidation film or a protective film is formed, for example.

1.5.3) Third Example

Figure 11:
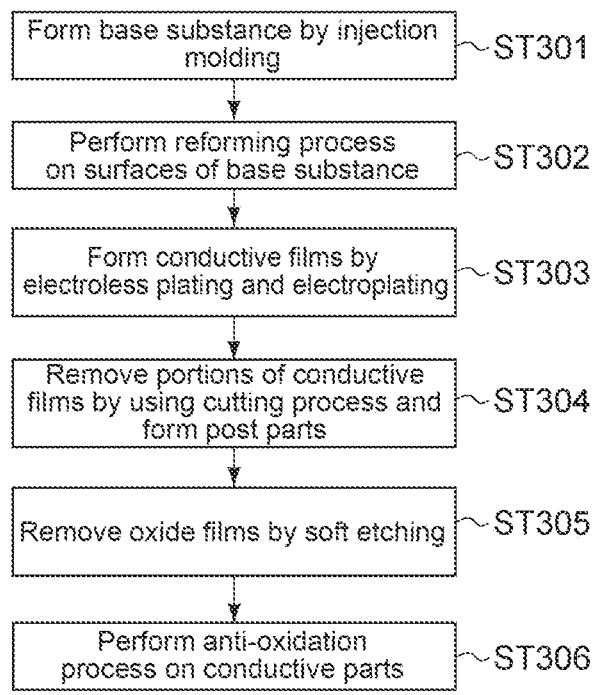
FIG. 11 is a flowchart illustrating a method for producing an MID according to a third example.

FIG. 11 is a flowchart illustrating a method for producing an MID according to a third example. ST 301 to ST 305 are the same processes as ST 101 to ST 105. ST 306 is the same processes as ST 208.

1.5.4) Fourth Example

Figure 12:
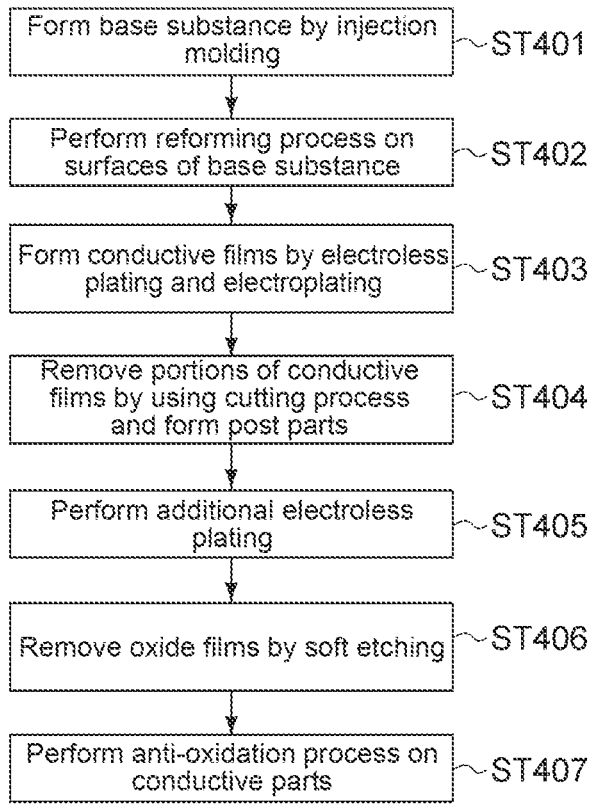
FIG. 12 is a flowchart illustrating a method for producing an MID according to a fourth example.

FIG. 12 is a flowchart illustrating a method for producing an MID according to a fourth example. ST 401 to ST 406 are the same processes as ST 201 to ST 206 described above. ST 407 is the same processes as ST 208.

1.5.5) Fifth Example

Figure 13:
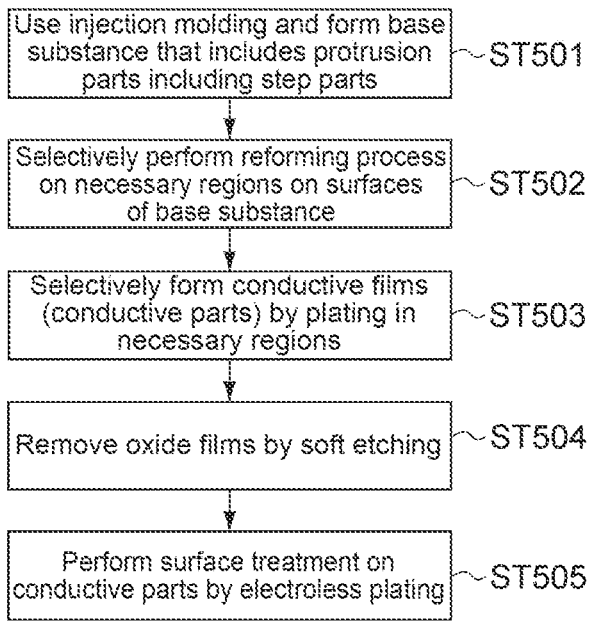
FIG. 13 is a flowchart illustrating a method for producing an MID according to a fifth example.

It is also possible to perform the following process if the conductive parts 33*a* are arranged (the electrode pads 16 and the electrode terminals are arranged) in a certain way. FIG. 13 is a flowchart illustrating a method for producing an MID according to a fifth example.

A base substance (that includes a base 31 and) that includes protrusion parts 33*d* including step parts 33*c* is formed by injection molding (St 501). At this time, the injection molding also makes through holes 33*b*. Here, the step parts 33*c* are not necessarily formed. As described above, it is also possible to form protrusion parts with high aspect ratios by the injection molding.

A reforming process is selectively performed on a necessary region on a surface of the base substance, that is, a region in which conductive parts 33*a* are mainly disposed (ST 502).

Conductive films (conductive parts 33*a*) are selectively formed by plating in the necessary region (ST 503). In this case, the plating may be electro plating or electroless plating using a mask.

Alternatively, the plating may be both the electro plating and the electroless plating.

ST 504 and ST 505 are the same processes as ST 105 and ST 106. Instead of the ST 504 and ST 505, it is also possible to perform ST 205 to ST 208 or ST 405 to ST 407.

When using this production method, it is possible to omit the cutting process.

1.5.6) Sixth Example

Figure 14:
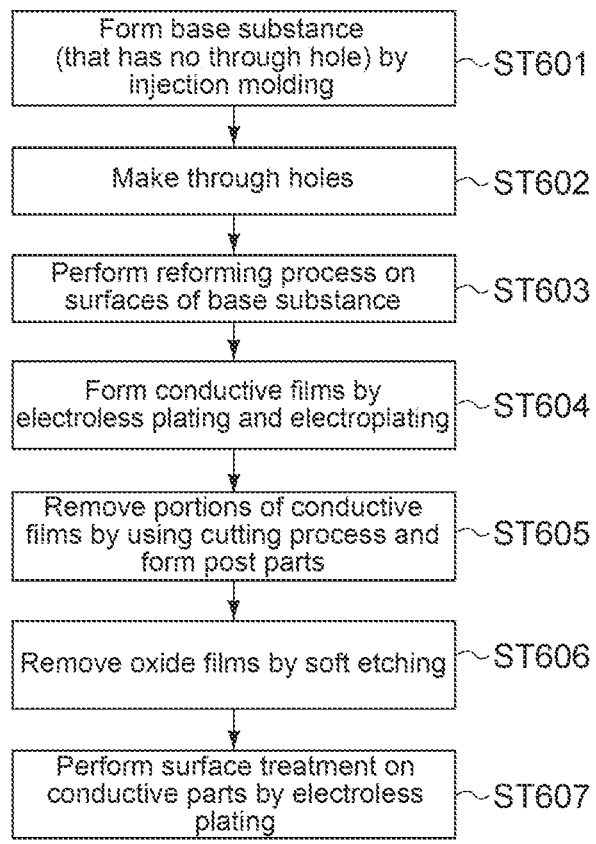
FIG. 14 is a flowchart illustrating a method for producing an MID according to a sixth example.

FIG. 14 is a flowchart illustrating a method for producing an MID according to a sixth example. A base substance that includes protrusion parts but has no through hole is formed by injection molding (ST 601). In a next step, through holes 33*b* are made (ST 602). The through holes 33*b* are made through mechanical processing such as laser processing, for example.

ST 603 to ST 607 are the same processes as ST 102 to ST 106. Instead of the ST 603 to ST 607, it is also possible to perform ST 202 to ST 208, ST 302 to ST 306, or ST 402 to ST 407.

1.5.7) Seventh Example

Figure 15:
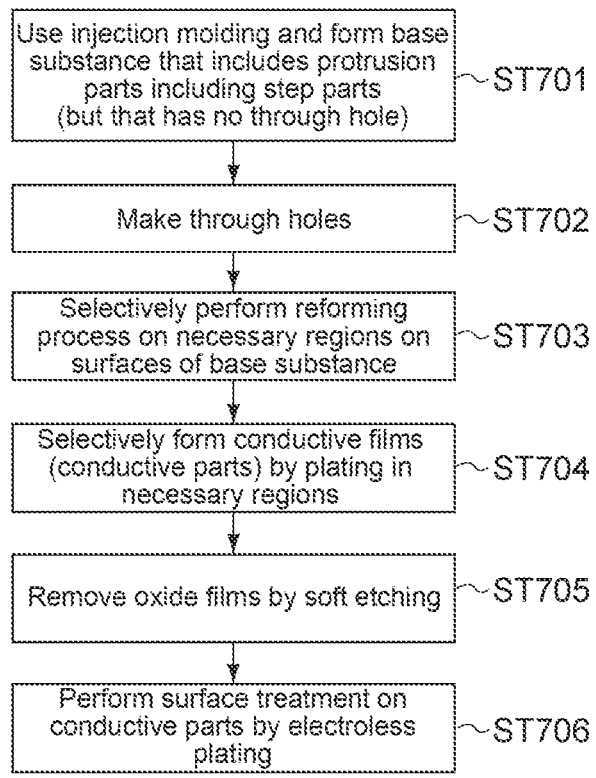
FIG. 15 is a flowchart illustrating a method for producing an MID according to a seventh example.

FIG. 15 is a flowchart illustrating a method for producing an MID according to a seventh example. A base (that includes a base substance 31 and) that includes protrusion parts including step parts but that has no through hole is formed by injection molding (ST 701). Next, through holes 33*b* are made in a way similar to ST 602 (ST 702).

ST 703 to ST 706 are the same processes as ST 502 to ST 505.

2. Second Embodiment

2.1) Configuration of MID

Figure 16A:
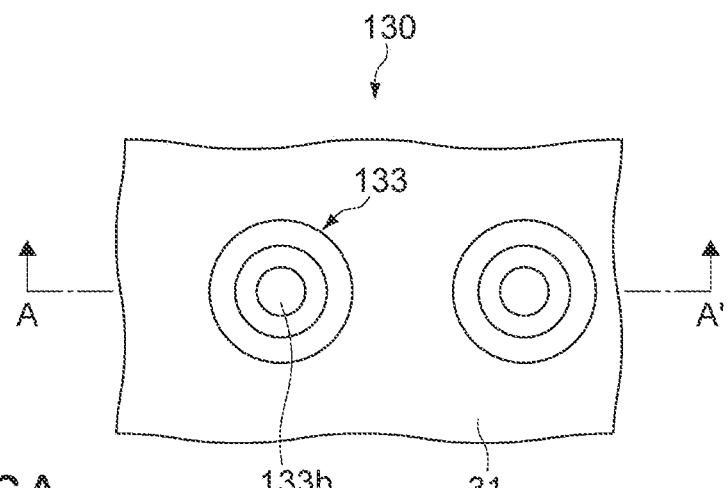
FIG. 16A is an enlarged plan view of a portion of an MID according to a second embodiment that is another embodiment.
Figure 16B:
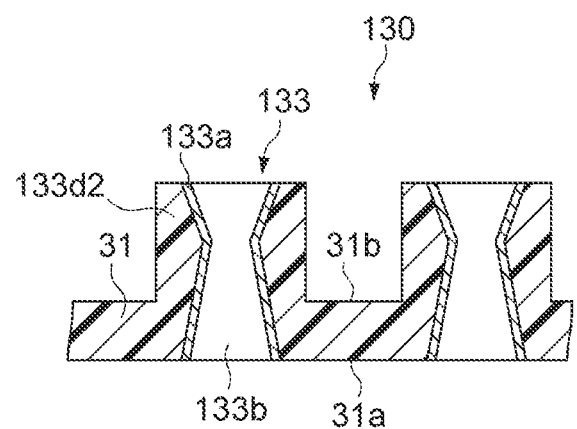
FIG. 16B is a cross-sectional view of the portion of the MID taken along a line A-A' of FIG. 16A.

FIG. 16A is an enlarged plan view of a portion of an MID according to a second embodiment that is another embodiment. FIG. 16B is a cross-sectional view of the portion of the MID taken along a line A-A' of FIG. 16A. In the description below, the structural elements that are to the same as the structural elements of the MID 30 according to (the example illustrated in FIG. 3A and FIG. 3B of) the above-described first embodiment are denoted by the same reference signs as the first embodiment, and description thereof will be omitted or simplified and their differences will be mainly described.

An MID 130 according to this embodiment is configured in a manner that axis centers of through holes 133*b* coincide with axis centers of post parts 133. In other words, the axis centers of the through holes 133*b* pass through substantial centers of solder (not illustrated here). When the positions of the through holes 133*b* are appropriately adjusted as described above, it is possible to appropriately adjust rigidities of the post parts 133.

In addition, the post parts 133 are disposed in a manner that they protrude from only one of the surfaces of the base 31. In this embodiment, component-side protrusion parts 133*d*2 stand on a second surface 31*b* of the base 31 that faces the electronic component (such as the image sensor 20). In the case where main material of the MID 130 is resin, difference in coefficients of thermal expansion between the MID 130 and the substrate 10 is smaller than difference in coefficients of thermal expansion between the MID 130 and the image sensor 20. This results in no substantial damage in the solder interposed between the substrate 10 and the MID 130 as described above with regard to the testing (see FIG. 5). Therefore, it is not necessary to form post parts on the first surface 31*a* side of the base 31 like this embodiment.

2.2) Method for Producing MID

Methods for producing an MID 130 according to the second embodiment are the same as the methods for producing the MID 30 according to the first embodiment described above. Any of the first to seventh examples are applicable to the second embodiment.

Figure 17A:
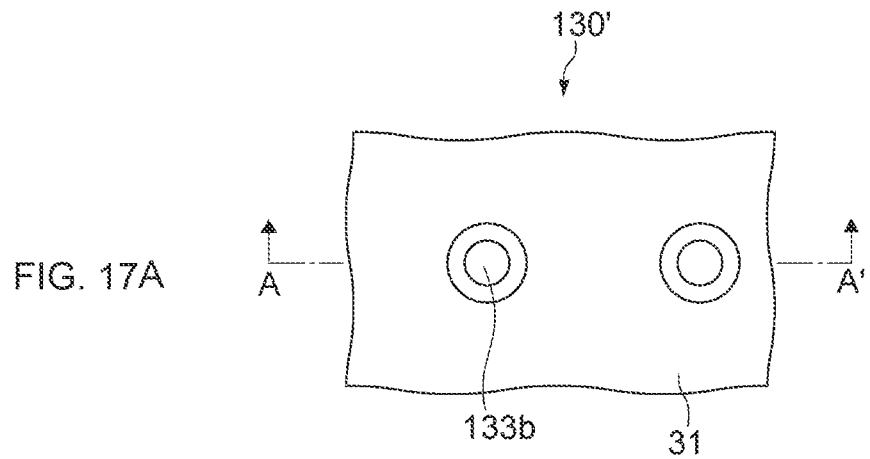
FIG. 17A and FIG. 17B are respectively a plan view and a cross-sectional view of a base substance having through holes.
Figure 17B:
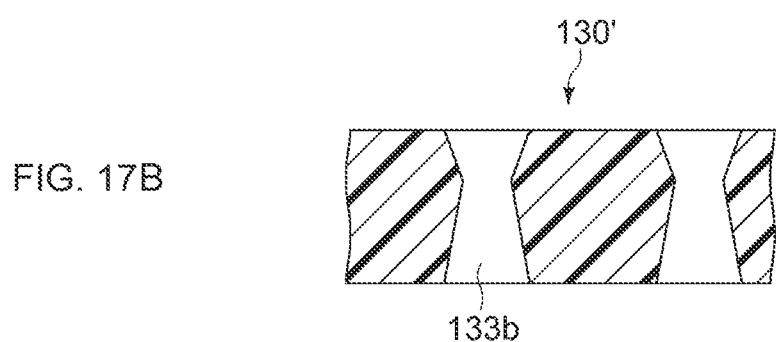
Figure 17C:
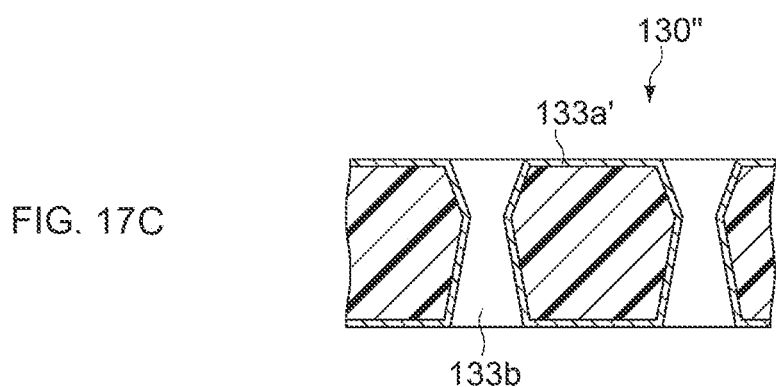
FIG. 17C is a cross-sectional view of the base substance with surfaces on which conductive films are formed.

FIG. 17A and FIG. 17B are respectively a plan view and a cross-sectional view of a base substance 130' that is formed by injection molding and that has through holes 133*b*. FIG. 17C is a cross-sectional view of a base substance 130" with surfaces on which conductive films 133*a*' are formed by electroless plating. The post parts 133 are formed as illustrated in FIG. 16A and FIG. 16B by cutting predetermined regions or the like around the through holes 133*b*. In addition, the cutting also removes portions of the conductive films 133*a*' and forms conductive parts 133*a*.

3. Third Embodiment

Figure 18:
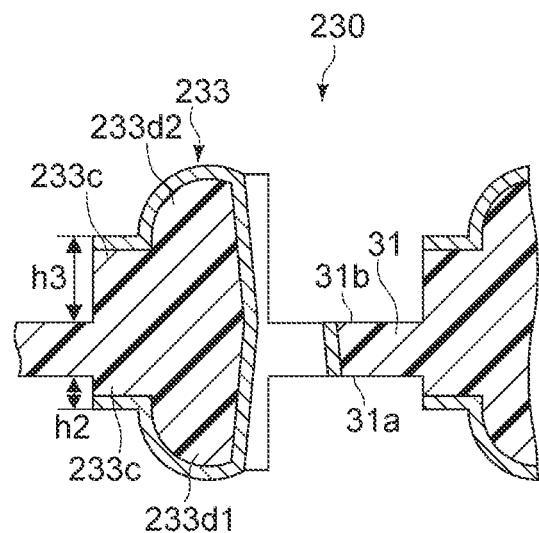
FIG. 18 is a cross-sectional view of an MID according to a third embodiment.

FIG. 18 is a cross-sectional view of an MID according to a third embodiment. With regard to post parts 233 of an MID 230, height h2 of substrate-side protrusion parts 233*d*1 is different from height h3 of component-side protrusion parts 233d2. For example, step parts 233c formed by cutting have different heights between the substrate-side protrusion parts 233d1 and the component-side protrusion parts 233d2. Specifically, the height h3 of step parts 233c on the second surface 31b side is higher than the height h2 of step parts 233c on the first surface 31a side.

As described above, in the case where main material of the MID 230 is resin, difference in coefficients of thermal expansion between the MID 230 and the substrate 10 is small, and there is no substantial damage in the solder interposed between the substrate 10 and the MID 230. Therefore, it is possible to form the protrusion parts in a manner that the height of the component-side protrusion parts 233d2 is lower than the height of the substrate-side protrusion parts 233d1 as described in this embodiment.

4. Fourth Embodiment

Figure 19:
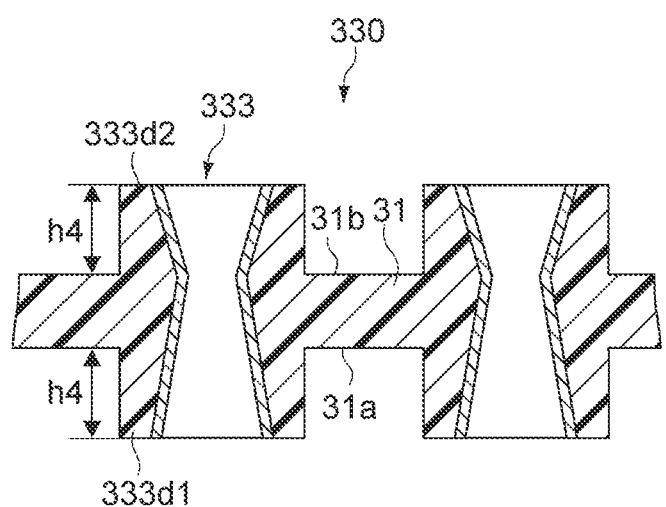
FIG. 19 is a cross-sectional view of an MID according to a fourth embodiment.

FIG. 19 is a cross-sectional view of an MID according to a fourth embodiment. An MID 330 is a modification of the second embodiment described above (see FIG. 16A and FIG. 16B). With regard to post parts 333 of the MID 330, height h4 of substrate-side protrusion parts 333d1 is the same as height h4 of component-side protrusion parts 333d2.

4A. Fifth Embodiment

In the first to fourth embodiments described above, the examples in which the through holes are made for respective protrusion parts have been described. However, it is also possible to make a single shared through hole for a plurality of protrusion parts.

Figure 27:
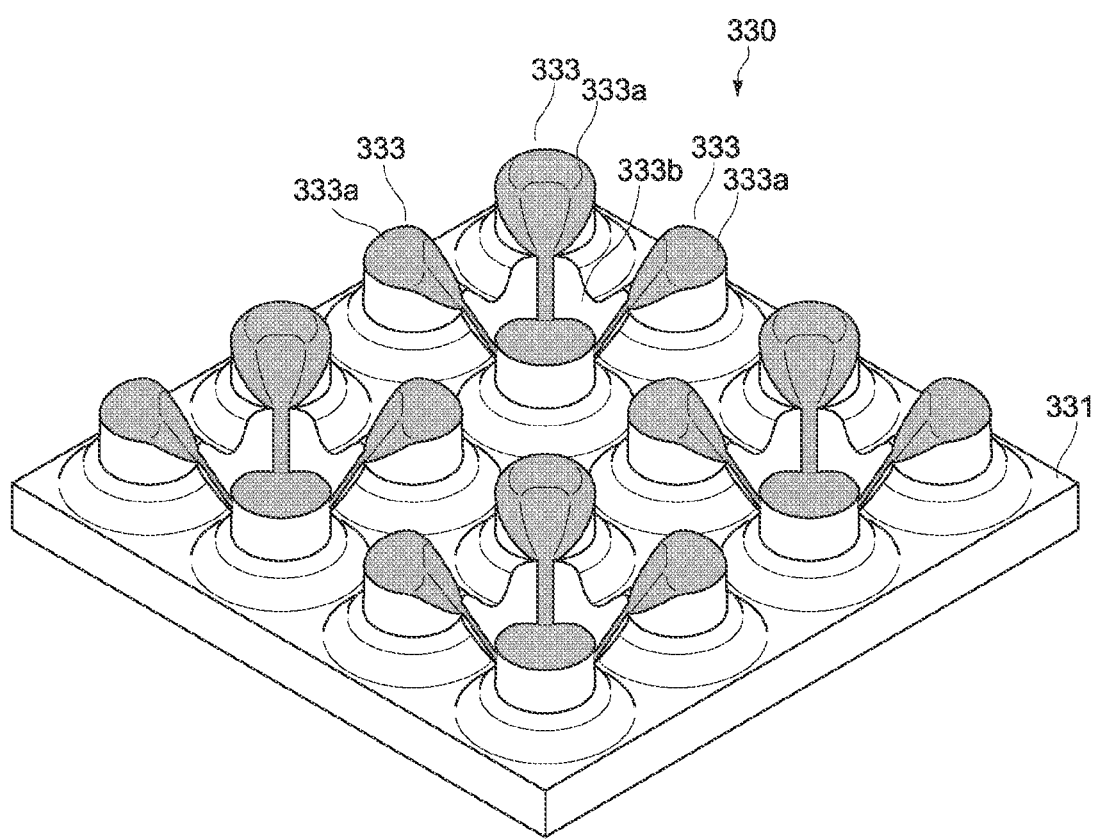
FIG. 27 is a perspective view of an MID according to a fifth embodiment when viewed from a component side.
Figure 28:
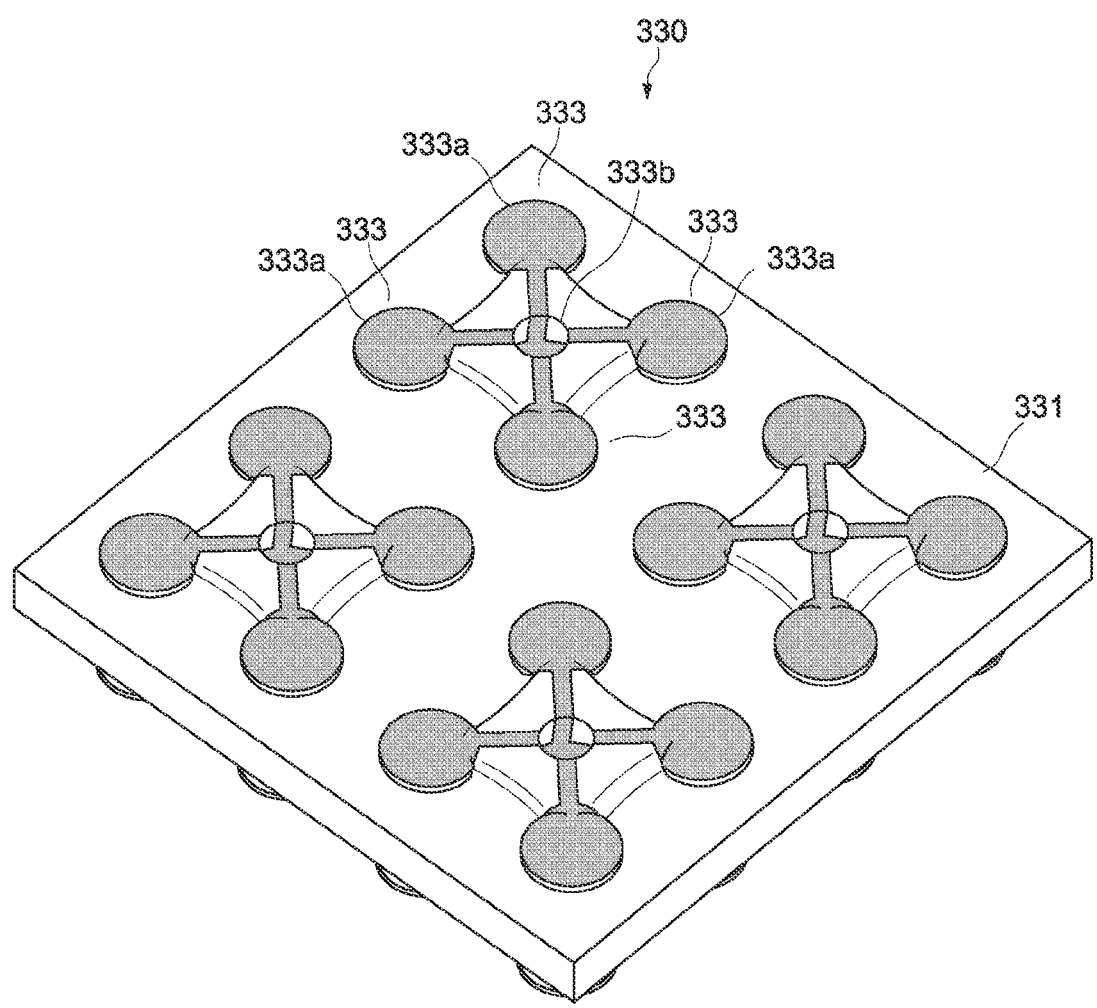
FIG. 28 is a perspective view of the MID according to the fifth embodiment when viewed from a substrate side.
Figure 29:
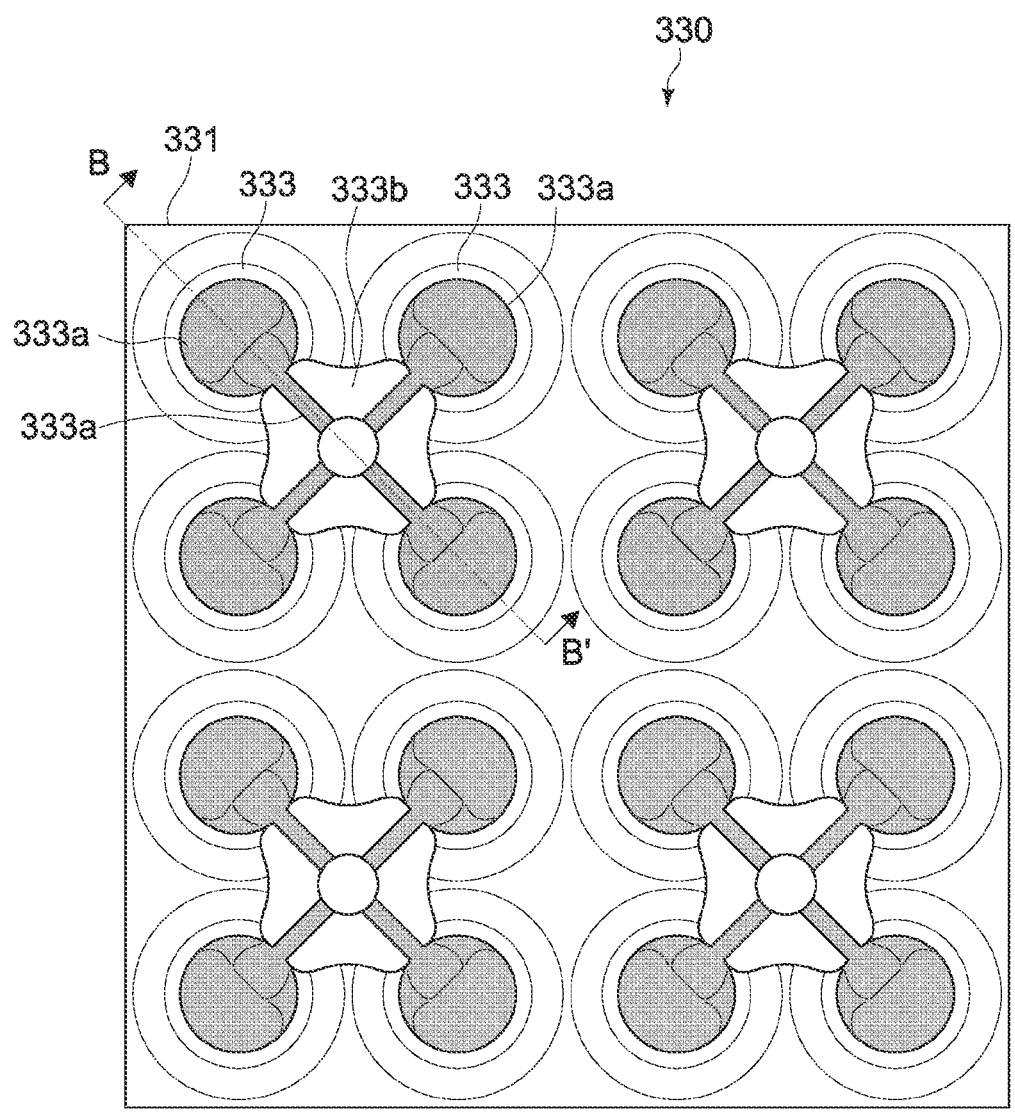
FIG. 29 is a plan view of the MID according to the fifth embodiment when viewed from the component side.
Figure 30:
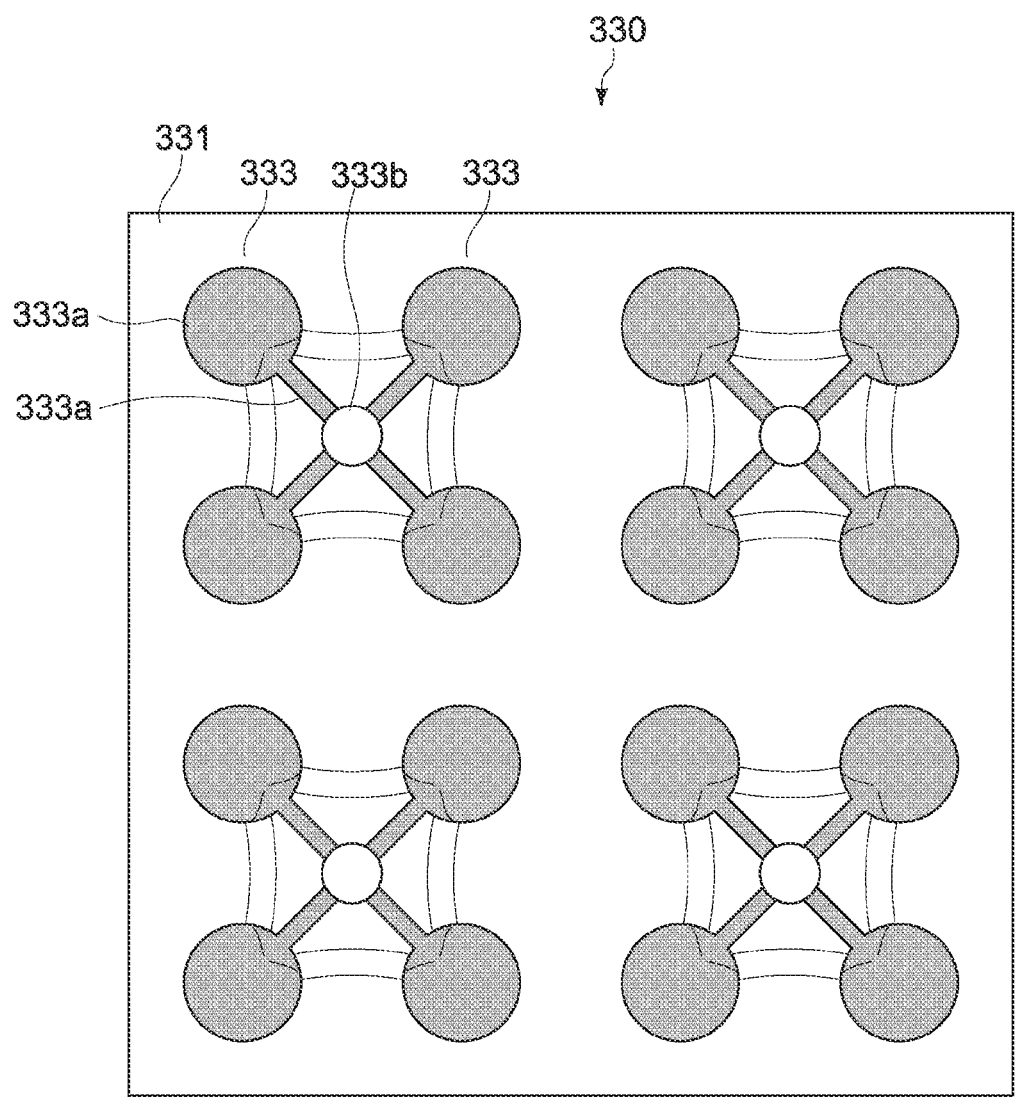
FIG. 30 is a plan view of the MID according to the fifth embodiment when viewed from the substrate side.
Figure 31:
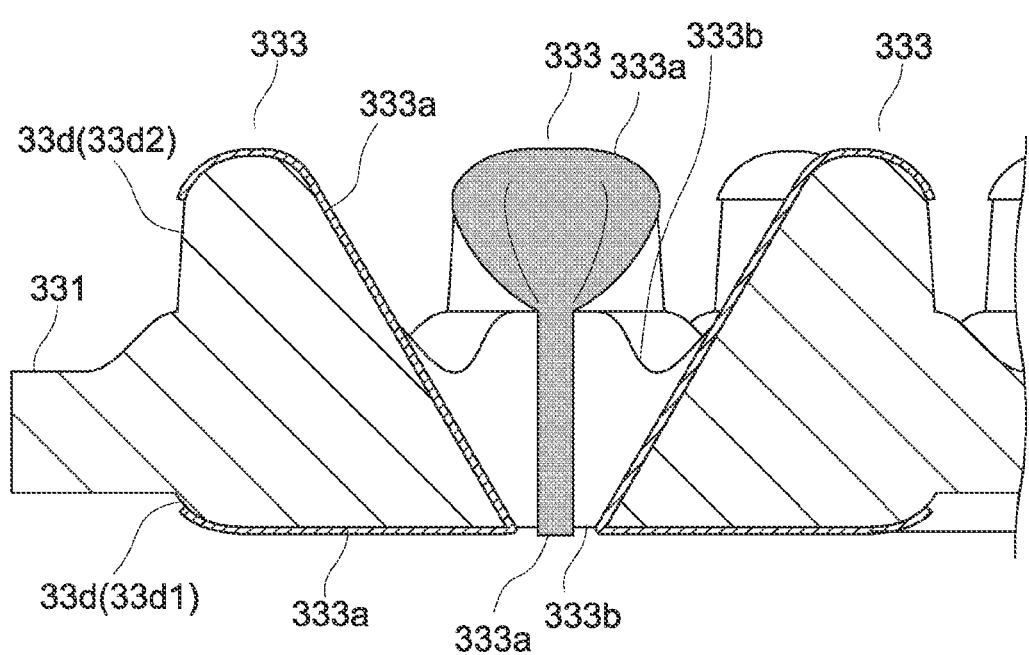
FIG. 31 is a cross-sectional view of the MID according to the fifth embodiment.

FIG. 27 is a perspective view of an MID 330 according to a fifth embodiment when viewed from a component side. FIG. 28 is a perspective view of the MID 330 when viewed from a substrate side. FIG. 29 is a plan view of the MID 330 when viewed from the component side. FIG. 30 is a plan view of the MID 330 when viewed from the substrate side. FIG. 31 is a cross-sectional view of the MID 330 taken along a line B-B' of FIG. 29.

With regard to the MID 330 according to the fifth embodiment, one through hole 333b is made for four post parts 333 (2×2 post parts in vertical and horizontal directions) in a group of the post parts 333 that are disposed in a matrix. The through hole 333b is made at a middle of the four post parts 333 (2×2 post parts 333 in the vertical and horizontal directions) on a plane.

With regard to the MID 330 according to the fifth embodiment, component-side protrusion parts 33d2 and substrate-side protrusion parts 33d1 of the post parts 333 are vertically asymmetrical to each other. Side surfaces on the through hole 333b side of the component-side protrusion parts 33d2 and side surfaces on the through hole 333b side of the substrate-side protrusion parts 33d1 form inclination at a constant angle from vertices of the component-side protrusion parts 33d2 to vertices of the substrate-side protrusion parts 33d1. This makes it possible to make the through hole 333b having an inverted conical shape in a manner that its diameter continuously decreases from the vertices of the component-side protrusion parts 33d2 toward the vertices (bottom vertices) of the substrate-side protrusion parts 33d1.

For example, the conductive parts 333a are formed by metal plating on a surface between the component-side protrusion parts 33d2 of the post parts 333 and the substrate-side protrusion parts 33d1 via the side surface of the through hole 333b. The conductive parts 333a electrically connect electrode pads 16 and the substrate 10 to electrode terminals 26 of the image sensor 20 as illustrated in FIG. 1. In this embodiment, four conductive parts 333a that are electrically independent are ensured by the single through hole 333b.

Here, the metal plating can be performed by using the method described in the fifth example. In other words, it is possible to form the metal plating by selectively reform surface portions of the component-side protrusion parts 33d2, surface portions of the substrate-side protrusion parts 33d1, and resin surfaces of wiring parts for connecting the surface portions by using a laser or the like, and selectively plating the reformed portions.

In this embodiment, the through hole 333b is made in a region surrounded by the plurality of post parts 333. This makes it possible to ensure planar distances between the post parts 333 and the through hole 333b as long as possible, and this makes it possible to moderate inclinations from the vertices of the component-side protrusion parts 33d2 of the post parts 333 toward the vertices (bottom vertices) of the substrate-side protrusion parts 33d1. Accordingly, it is possible to easily take out molded resin from a mold in the case where the resin is molded by injection molding by using the mold. In addition, workability of laser irradiation is improved because of the moderate inclinations of laser irradiation parts in the case where metal plating target regions are reformed by using a laser, for example.

Note that, the example in which the protrusion parts 33 are formed in a manner that the height of the substrate-side protrusion parts 33d1 from the base 331 is shorter than the height of the component-side protrusion parts 33d2 from the base 331 has been described in this embodiment. However, the respective heights may be appropriately changed depending on materials of the substrate or the component.

5. Modifications

The present technology is not limited to the above-described embodiments. Various other embodiments can be achieved.

The base substance having at least the protrusion parts has been formed by injection molding in accordance with the above-described production methods. However, it is also possible to form the protrusion parts by cutting a plate-like base substance without using the injection molding, perform predetermined processes, and then form step parts through cutting. Alternatively, it is also possible to form post parts without the step parts by cutting the plate-like base substance after predetermined processes. In such cases, through holes may also be formed by cutting, or a base substance that has only through holes may be formed first of all by injection molding.

In the above-described embodiments, the height of the component-side protrusion parts of the post parts is the same as the substrate-side protrusion parts of the post parts or is higher than the substrate-side protrusion parts of the post parts. However, the protrusion parts may be formed in a manner that the height of the substrate-side protrusion parts is higher than the component-side protrusion parts depending on main material of the electronic component or main material of the electrode array structure of the electronic component.

In the above-described embodiments, the image sensor 20 is used as an example of the electronic component. However, the electronic component may be another sensor, a wafer-level chip scale packaging (WL-CSP) component, or another electronic component. In the case of the WL-CSP component, typical main material of the WL-CSP component is single-crystal silicon.

A region between the substrate 10 and the MID may be configured by solidifying underfill to maintain high rigidity.

The image sensor module according to the present technology is applicable not only to cameras used by general end users but also to professional-quality cameras used by broadcasting professionals. In future, it is expected that image sensors get larger with enhancement in high-resolution video, this results in relative increase in amounts of thermal distortion due to heat generated at times of driving, and larger stress is applied to soldered parts. Therefore, the present technology is an essential technology to alleviate stress applied to the soldered parts and ensure long-term reliability when using cameras for a long time.

Out of the feature parts according to the respective embodiments described above, at least two feature parts can be combined.

6. Application Examples of Present Technology 6.1) First Application Example

The technology according to the disclosure can be applied to various products. For example, the image sensor module including the MID according to each of the above-described embodiments may be used as an image sensor module installed in an endoscope in a medical field.

Figure 20:
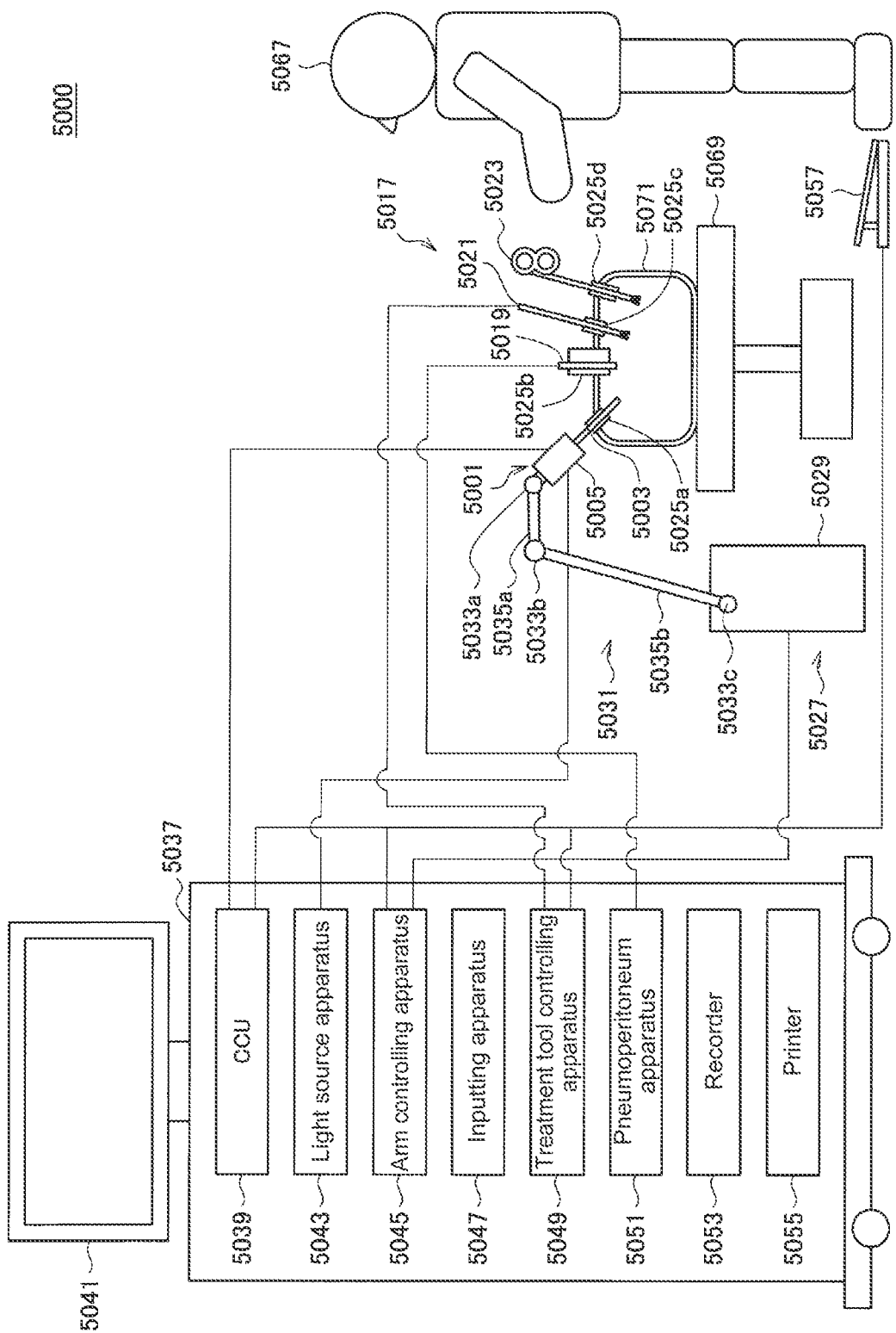
FIG. 20 is a diagram illustrating an example of a schematic configuration of an endoscopic surgery system.

FIG. 20 is a diagram depicting an example of a schematic configuration of an endoscopic surgery system 5000 to which the technology according to the present disclosure can be applied. In FIG. 20, a state is illustrated in which a surgeon (medical doctor) 5067 is using the endoscopic surgery system 5000 to perform surgery for a patient 5071 on a patient bed 5069. As depicted, the endoscopic surgery system 5000 includes an endoscope 5001, other surgical tools 5017, a supporting arm apparatus 5027 which supports the endoscope 5001 thereon, and a cart 5037 on which various apparatus for endoscopic surgery are mounted.

In endoscopic surgery, in place of incision of the abdominal wall to perform laparotomy, a plurality of tubular aperture devices called trocars 5025 a to 5025 d are used to puncture the abdominal wall. Then, a lens barrel 5003 of the endoscope 5001 and the other surgical tools 5017 are inserted into a body cavity of the patient 5071 through the trocars 5025 a to 5025 d. In the example depicted, as the other surgical tools 5017, a pneumoperitoneum tube 5019, an energy device 5021 and forceps 5023 are inserted into a body cavity of the patient 5071. Further, the energy device 5021 is a treatment tool for performing incision and peeling of a tissue, sealing of a blood vessel or the like by high frequency current or ultrasonic vibration. However, the surgical tools 5017 depicted are mere examples at all, and as the surgical tools 5017, various surgical tools which are generally used in endoscopic surgery such as, for example, tweezers or a retractor may be used.

An image of a surgical region in a body cavity of the patient 5071 captured by the endoscope 5001 is displayed on a display apparatus 5041. The surgeon 5067 would use the energy device 5021 or the forceps 5023 while watching the image of the surgical region displayed on the display apparatus 5041 on the real time basis to perform such treatment as, for example, resection of an affected area. It is to be noted that, though not depicted, the pneumoperitoneum tube 5019, the energy device 5021, and the forceps 5023 are supported by the surgeon 5067, an assistant, or the like during surgery.

(Supporting Arm Apparatus)

The supporting arm apparatus 5027 includes an arm unit 5031 extending from a base unit 5029. In the example depicted, the arm unit 5031 includes joint portions 5033 a, 5033 b and 5033 c and links 5035 a and 5035 b and is driven under the control of an arm controlling apparatus 5045. The endoscope 5001 is supported by the arm unit 5031 such that the position and the posture of the endoscope 5001 are controlled. Consequently, stable fixation in position of the endoscope 5001 can be implemented.

(Endoscope)

The endoscope 5001 includes the lens barrel 5003 which has a region of a predetermined length from a distal end thereof to be inserted into a body cavity of the patient 5071, and a camera head 5005 connected to a proximal end of the lens barrel 5003. In the example depicted, the endoscope 5001 is depicted as a rigid endoscope having the lens barrel 5003 of the hard type. However, the endoscope 5001 may otherwise be configured as a flexible endoscope having the lens barrel 5003 of the flexible type.

The lens barrel 5003 has, at a distal end thereof, an opening in which an objective lens is fitted. A light source apparatus 5043 is connected to the endoscope 5001 such that light generated by the light source apparatus 5043 is introduced to a distal end of the lens barrel by a light guide extending in the inside of the lens barrel 5003 and is radiated toward an observation target in a body cavity of the patient 5071 through the objective lens. It is to be noted that the endoscope 5001 may be a forward-viewing endoscope or may be an oblique-viewing endoscope or a side-viewing endoscope.

An optical system and an image pickup element are provided in the inside of the camera head 5005 such that reflected light (observation light) from an observation target is condensed on the image pickup element by the optical system. The observation light is photoelectrically converted by the image pickup element to generate an electric signal corresponding to the observation light, namely, an image signal corresponding to an observation image. The image signal is transmitted as RAW data to a camera control unit (CCU) 5039. It is to be noted that the camera head 5005 has a function incorporated therein for suitably driving the optical system of the camera head 5005 to adjust the magnification and the focal length.

It is to be noted that, in order to establish compatibility with, for example, a stereoscopic vision (3D display), a plurality of image pickup elements may be provided on the camera head 5005. In this case, a plurality of relay optical systems is provided in the inside of the lens barrel 5003 in order to guide observation light to each of the plurality of image pickup elements.

(Various Apparatus Incorporated in Cart)

The CCU 5039 includes a central processing unit (CPU), a graphics processing unit (GPU) or the like and integrally controls operation of the endoscope 5001 and the display apparatus 5041. In particular, the CCU 5039 performs, for an image signal received from the camera head 5005, various image processes for displaying an image based on the image signal such as, for example, a development process (demosaic process). The CCU 5039 provides the image signal for which the image processes have been performed to the display apparatus 5041. Further, the CCU 5039 transmits a control signal to the camera head 5005 to control driving of the camera head 5005. The control signal may include information relating to an image pickup condition such as a magnification or a focal length.

The display apparatus 5041 displays an image based on an image signal for which the image processes have been performed by the CCU 5039 under the control of the CCU 5039. If the endoscope 5001 is ready for imaging of a high resolution such as 4K (horizontal pixel number 3840× vertical pixel number 2160), 8K (horizontal pixel number 7680×vertical pixel number 4320) or the like and/or ready for 3D display, then a display apparatus by which corresponding display of the high resolution and/or 3D display are possible may be used as the display apparatus 5041. Where the apparatus is ready for imaging of a high resolution such as 4K or 8K, if the display apparatus used as the display apparatus 5041 has a size of equal to or not less than 55 inches, then a more immersive experience can be obtained. Further, a plurality of the display apparatuses 5041 having different resolutions and/or different sizes may be provided in accordance with purposes.

The light source apparatus 5043 includes a light source such as, for example, a light emitting diode (LED) and supplies irradiation light for imaging of a surgical region to the endoscope 5001.

The arm controlling apparatus 5045 includes a processor such as, for example, a CPU and operates in accordance with a predetermined program to control driving of the arm unit 5031 of the supporting arm apparatus 5027 in accordance with a predetermined controlling method.

An inputting apparatus 5047 is an input interface for the endoscopic surgery system 5000. A user can input various kinds of information or instructions to the endoscopic surgery system 5000 through the inputting apparatus 5047. For example, the user would input various kinds of information relating to surgery such as physical information of a patient, information regarding a surgical procedure of the surgery and so forth through the inputting apparatus 5047. Further, the user would input, for example, an instruction to drive the arm unit 5031, an instruction to change an image pickup condition (type of irradiation light, magnification, focal length or the like) of the endoscope 5001, an instruction to drive the energy device 5021, or the like through the inputting apparatus 5047.

The type of the inputting apparatus 5047 is not limited and may be any one of various known inputting apparatus. As the inputting apparatus 5047, for example, a mouse, a keyboard, a touchscreen, a switch, a foot switch 5057, a lever, and/or the like may be applied. Where the touchscreen is used as the inputting apparatus 5047, it may be provided on the display surface of the display apparatus 5041.

Otherwise, the inputting apparatus 5047 is a device to be mounted on a user such as, for example, a glasses type wearable device or a head mounted display (HMD), and various kinds of inputting are performed in response to a gesture or a line of sight of the user detected by any of the devices mentioned. Further, the inputting apparatus 5047 includes a camera which can detect a motion of a user, and various kinds of inputting are performed in response to a gesture or a line of sight of the user detected from a video taken by the camera. Further, the inputting apparatus 5047 includes a microphone which can collect voice of a user, and various kinds of inputting are performed by voice collected by the microphone. By configuring the inputting apparatus 5047 such that various kinds of information can be input in a contactless fashion in this manner, especially a user who belongs to a clean area (for example, the surgeon 5067) can operate an apparatus belonging to an unclean area in a contactless fashion. Further, since the user can operate an apparatus without releasing a possessed surgical tool from his/her hand, the convenience to the user is improved.

A treatment tool controlling apparatus 5049 controls driving of the energy device 5021 for cautery or incision of a tissue, sealing of a blood vessel or the like. A pneumoperitoneum apparatus 5051 feeds gas into a body cavity of the patient 5071 through the pneumoperitoneum tube 5019 to inflate the body cavity in order to secure the field of view of the endoscope 5001 and secure the working space for the surgeon. A recorder 5053 is an apparatus capable of recording various kinds of information relating to surgery. A printer 5055 is an apparatus capable of printing various kinds of information relating to surgery in various forms such as a text, an image or a graph.

In the following, especially a characteristic configuration of the endoscopic surgery system 5000 is described in more detail.

(Supporting Arm Apparatus)

The supporting arm apparatus 5027 includes the base unit 5029 serving as a base stand, and the arm unit 5031 extending from the base unit 5029. In the example depicted, the arm unit 5031 includes the plurality of joint portions 5033 a, 5033 b and 5033 c and the plurality of links 5035 a and 5035 b connected to each other by the joint portion 5033 b. In FIG. 20, for simplified illustration, the configuration of the arm unit 5031 is depicted in a simplified form. Actually, the shape, number and arrangement of the joint portions 5033 a to 5033 c and the links 5035 a and 5035 b and the direction and so forth of axes of rotation of the joint portions 5033 a to 5033 c can be set suitably such that the arm unit 5031 has a desired degree of freedom. For example, the arm unit 5031 may favorably be configured such that it has a degree of freedom equal to or not less than 6 degrees of freedom. This makes it possible to move the endoscope 5001 freely within the movable range of the arm unit 5031. Consequently, it becomes possible to insert the lens barrel 5003 of the endoscope 5001 from a desired direction into a body cavity of the patient 5071.

An actuator is provided in each of the joint portions 5033 a to 5033 c, and the joint portions 5033 a to 5033 c are configured such that they are rotatable around predetermined axes of rotation thereof by driving of the respective actuators. The driving of the actuators is controlled by the arm controlling apparatus 5045 to control the rotational angle of each of the joint portions 5033 a to 5033 c thereby to control driving of the arm unit 5031. Consequently, control of the position and the posture of the endoscope 5001 can be implemented. Thereupon, the arm controlling apparatus 5045 can control driving of the arm unit 5031 by various known controlling methods such as force control or position control.

For example, if the surgeon 5067 suitably inputs operation through the inputting apparatus 5047 (including the foot switch 5057), then driving of the arm unit 5031 may be controlled suitably by the arm controlling apparatus 5045 in response to the input operation to control the position and the posture of the endoscope 5001. After the endoscope 5001 at the distal end of the arm unit 5031 is moved from any position to any different position by the control just described, the endoscope 5001 can be supported fixedly at the position after the movement. It is to be noted that the arm unit 5031 may be operated in a so-called master-slave fashion. In this case, the arm unit 5031 may be remotely controlled by the user through the inputting apparatus 5047 which is placed at a place remote from the operating room.

Further, where force control is applied, the arm controlling apparatus 5045 may perform power-assisted control to drive the actuators of the joint portions 5033 a to 5033 c such that the arm unit 5031 may receive external force from the user and move smoothly following the external force. This makes it possible to move, when the user directly touches and moves the arm unit 5031, the arm unit 5031 with comparatively weak force. Accordingly, it becomes possible for the user to move the endoscope 5001 more intuitively by a simpler and easier operation, and the convenience to the user can be improved.

Here, generally in endoscopic surgery, the endoscope 5001 is supported by a medical doctor called scopist. In contrast, where the supporting arm apparatus 5027 is used, the position of the endoscope 5001 can be fixed more certainly without hands, and therefore, an image of a surgical region can be obtained stably and surgery can be performed smoothly.

It is to be noted that the arm controlling apparatus 5045 may not necessarily be provided on the cart 5037. Further, the arm controlling apparatus 5045 may not necessarily be a single apparatus. For example, the arm controlling apparatus 5045 may be provided in each of the joint portions 5033 *a* to 5033 *c* of the arm unit 5031 of the supporting arm apparatus 5027 such that the plurality of arm controlling apparatus 5045 cooperates with each other to implement driving control of the arm unit 5031.

(Light Source Apparatus)

The light source apparatus 5043 supplies irradiation light for imaging a surgical region to the endoscope 5001. The light source apparatus 5043 includes a white light source which includes, for example, an LED, a laser light source or a combination of them. In this case, where the white light source includes a combination of RGB laser light sources, since the output intensity and the output timing can be controlled with a high degree of accuracy for each color (each wavelength), adjustment of the white balance of a captured image can be performed by the light source apparatus 5043. Further, in this case, if laser light beams from the respective RGB laser light sources are radiated time-divisionally on an observation target and driving of the image pickup element of the camera head 5005 is controlled in synchronism with the radiation timings, then images individually corresponding to the R, G and B colors can be captured time-divisionally. According to the method just described, a color image can be obtained even if a color filter is not provided for the image pickup element.

Further, driving of the light source apparatus 5043 may be controlled such that the intensity of light to be output is changed for each predetermined time. By controlling driving of the image pickup element of the camera head 5005 in synchronism with the timing of the change of the intensity of light to acquire images time-divisionally and synthesizing the images, an image of a high dynamic range free from so-called blocked-up shadows and blown-out highlights can be created.

Further, the light source apparatus 5043 may be configured to be capable of supplying light of a predetermined wavelength band corresponding to special light observation. In the special light observation, for example, by utilizing the wavelength dependency of absorption of light in a body tissue to radiate light (namely, white light) of a narrower wavelength band in comparison with irradiation light utilized upon ordinary observation, so-called narrow band light observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by radiation of excitation light may be performed. In the fluorescent observation, it is possible to perform observation of fluorescent light from a body tissue by radiating excitation light on the body tissue (autofluorescence observation), to obtain a fluorescent light image by locally injecting a reagent such as indocyanine green (ICG) into a body tissue and radiating excitation light corresponding to a fluorescent light wavelength of the reagent on the body tissue, or the like. The light source apparatus 5043 can be configured to supply narrow-band light and/or excitation light suitable for such special light observation.

(Camera Head and CCU)

Figure 21:
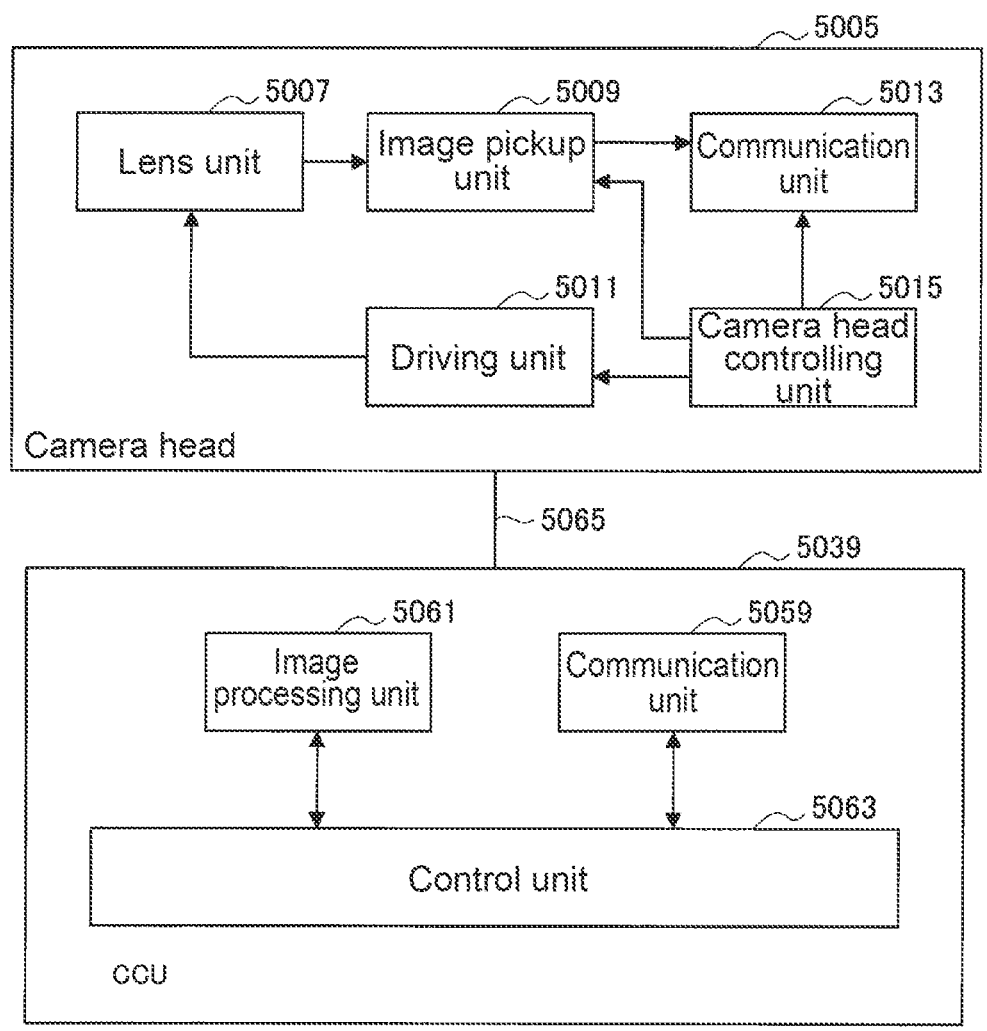
FIG. 21 is a block diagram illustrating an example of functional configurations of a camera head and a CCU illustrated in FIG. 20.

Functions of the camera head 5005 of the endoscope 5001 and the CCU 5039 are described in more detail with reference to FIG. 21. FIG. 21 is a block diagram depicting an example of a functional configuration of the camera head 5005 and the CCU 5039 depicted in FIG. 20.

Referring to FIG. 21, the camera head 5005 has, as functions thereof, a lens unit 5007, an image pickup unit 5009, a driving unit 5011, a communication unit 5013 and a camera head controlling unit 5015. Further, the CCU 5039 has, as functions thereof, a communication unit 5059, an image processing unit 5061 and a control unit 5063. The camera head 5005 and the CCU 5039 are connected to be bidirectionally communicable by a transmission cable 5065.

First, a functional configuration of the camera head 5005 is described. The lens unit 5007 is an optical system provided at a connecting location of the camera head 5005 to the lens barrel 5003. Observation light taken in from the distal end of the lens barrel 5003 is introduced into the camera head 5005 and enters the lens unit 5007. The lens unit 5007 includes a combination of a plurality of lenses including a zoom lens and a focusing lens. The lens unit 5007 has optical properties adjusted such that the observation light is condensed on a light receiving face of the image pickup element of the image pickup unit 5009. Further, the zoom lens and the focusing lens are configured such that the positions thereof on their optical axes are movable for adjustment of the magnification and the focal point of an image to be captured.

The image pickup unit 5009 includes an image pickup element and disposed at a succeeding stage to the lens unit 5007. Observation light having passed through the lens unit 5007 is condensed on the light receiving face of the image pickup element, and an image signal corresponding to the observation image is generated by photoelectric conversion. The image signal generated by the image pickup unit 5009 is provided to the communication unit 5013.

As the image pickup element which is included in the image pickup unit 5009, an image sensor, for example, of the complementary metal oxide semiconductor (CMOS) type is used which has a Bayer array and is capable of capturing a color image. It is to be noted that, as the image pickup element, an image pickup element may be used which is ready, for example, for capturing of an image of a high resolution equal to or not less than 4K. If an image of a surgical region is obtained in a high resolution, then the surgeon 5067 can comprehend a detailed state of the surgical region and can proceed with the surgery more smoothly.

Further, the image pickup element which is included in the image pickup unit 5009 includes a pair of image pickup elements for acquiring respective image signals for the right eye and the left eye compatible with 3D display. Where 3D display is applied, the surgeon 5067 can comprehend the depth of a living body tissue in the surgical region more accurately. It is to be noted that, if the image pickup unit 5009 is configured as an image pickup unit of the multi-plate type, then a plurality of systems of lens units 5007 is provided in a manner that the systems correspond to the respective image pickup elements.

In addition, the image pickup unit 5009 may not necessarily be provided on the camera head 5005. For example, the image pickup unit 5009 may be provided just behind the objective lens in the inside of the lens barrel 5003.

The driving unit 5011 includes an actuator and moves the zoom lens and the focusing lens of the lens unit 5007 by a predetermined distance along the optical axis under the control of the camera head controlling unit 5015. Consequently, the magnification and the focal point of an image to be captured by the image pickup unit 5009 can be adjusted suitably.

The communication unit 5013 includes a communication apparatus for transmitting and receiving various kinds of information to and from the CCU 5039. The communication unit 5013 transmits an image signal acquired from the image pickup unit 5009 as RAW data to the CCU 5039 through the transmission cable 5065. Thereupon, in order to display the captured image of the surgical region in low latency, favorably the image signal is transmitted by optical communication. This is because, upon surgery, the surgeon 5067 performs surgery while observing the state of the affected area through the captured image, and it is demanded for a moving image of the surgical region to be displayed on the real time basis as far as possible in order to achieve surgery with a higher degree of safety and certainty. Where optical communication is applied, a photoelectric conversion module for converting an electric signal into an optical signal is provided in the communication unit 5013. After the image signal is converted into an optical signal by the photoelectric conversion module, it is transmitted to the CCU 5039 through the transmission cable 5065.

Further, the communication unit 5013 receives a control signal for controlling driving of the camera head 5005 from the CCU 5039. The control signal includes information relating to image pickup conditions such as, for example, information that a frame rate of an image to be captured is designated, information that an exposure value of image capturing is designated, and/or information that a magnification and a focal point of an image to be captured are designated. The communication unit 5013 provides the received control signal to the camera head controlling unit 5015. It is to be noted that also the control signal from the CCU 5039 may be transmitted by optical communication. In this case, a photoelectric conversion module for converting an optical signal into an electric signal is provided in the communication unit 5013. After the control signal is converted into an electric signal by the photoelectric conversion module, the electric signal is provided to the camera head controlling unit 5015.

It is to be noted that the above-described image pickup conditions such as the frame rate, exposure value, magnification, and focal point are set automatically by the control unit 5063 of the CCU 5039 on the basis of an acquired image signal. In other words, an auto exposure (AE) function, an auto focus (AF) function and an auto white balance (AWB) function are incorporated in the endoscope 5001.

The camera head controlling unit 5015 controls driving of the camera head 5005 on the basis of a control signal received from the CCU 5039 through the communication unit 5013. For example, the camera head controlling unit 5015 controls driving of the image pickup element of the image pickup unit 5009 on the basis of the information that a frame rate of an image to be captured is designated and/or the information that exposure of image capturing is designated. Further, for example, the camera head controlling unit 5015 controls the driving unit 5011 to suitably move the zoom lens and the focusing lens of the lens unit 5007 on the basis of the information that a magnification and a focal point of an image to be captured are designated. The camera head controlling unit 5015 may further include a function for storing information for identifying the lens barrel 5003 or the camera head 5005.

It is to be noted that, by disposing the components such as the lens unit 5007 and the image pickup unit 5009 in a sealed structure having high airtightness and waterproof, the camera head 5005 can be provided with resistance to an autoclave sterilization process.

Now, a functional configuration of the CCU 5039 is described. The communication unit 5059 includes a communication apparatus for transmitting and receiving various kinds of information to and from the camera head 5005. The communication unit 5059 receives an image signal transmitted thereto from the camera head 5005 through the transmission cable 5065. Thereupon, the image signal may be transmitted favorably by optical communication as described above. In this case, for the compatibility with optical communication, the communication unit 5059 includes a photoelectric conversion module for converting an optical signal into an electric signal. The communication unit 5059 provides the image signal after conversion into an electric signal to the image processing unit 5061.

Further, the communication unit 5059 transmits, to the camera head 5005, a control signal for controlling driving of the camera head 5005. The control signal may also be transmitted by optical communication.

The image processing unit 5061 performs various image processes for an image signal in the form of RAW data transmitted thereto from the camera head 5005. The image processes include various known signal processes such as, for example, a development process, an image quality improving process (a bandwidth enhancement process, a super-resolution process, a noise reduction (NR) process and/or an image stabilization process) and/or an enlargement process (electronic zooming process). Further, the image processing unit 5061 performs a detection process for an image signal in order to perform the AE, AF and AWB.

The image processing unit 5061 includes a processor such as a CPU or a GPU, and when the processor operates in accordance with a predetermined program, the image processes and the detection process described above can be performed. It is to be noted that, where the image processing unit 5061 includes a plurality of GPUs, the image processing unit 5061 suitably divides information relating to an image signal such that image processes are performed in parallel by the plurality of GPUs.

The control unit 5063 performs various kinds of control relating to capturing of an image of a surgical region by the endoscope 5001 and display of the captured image. For example, the control unit 5063 generates a control signal for controlling driving of the camera head 5005. Thereupon, if image pickup conditions are input by the user, then the control unit 5063 generates a control signal on the basis of the input by the user. Alternatively, where the endoscope 5001 has the AE function, the AF function and the AWB function incorporated therein, the control unit 5063 suitably calculates an optimum exposure value, focal length and white balance in response to a result of the detection process performed by the image processing unit 5061 and generates a control signal.

Further, the control unit 5063 controls the display apparatus 5041 to display an image of a surgical region on the basis of an image signal for which image processes have been performed by the image processing unit 5061. Thereupon, the control unit 5063 recognizes various objects in the surgical region image using various image recognition technologies. For example, the control unit 5063 can recognize a surgical tool such as forceps, a particular living body region, bleeding, mist appeared when the energy device 5021 is used and so forth by detecting the shape, color and so forth of edges of objects included in the surgical region image. The control unit 5063 causes, when it controls the display unit 5041 to display a surgical region image, various kinds of surgery supporting information to be displayed in an overlapping manner with an image of the surgical region using a result of the recognition. Where the surgery supporting information is displayed in an overlapping manner and presented to the surgeon 5067, the surgeon 5067 can proceed with the surgery more safety and certainty.

The transmission cable 5065 which connects the camera head 5005 and the CCU 5039 to each other is an electric signal cable ready for communication of an electric signal, an optical fiber ready for optical communication, or a composite cable ready for both of electrical and optical communication.

Here, while, in the example depicted, communication is performed by wired communication using the transmission cable 5065, the communication between the camera head 5005 and the CCU 5039 may be performed otherwise by wireless communication. Where the communication between the camera head 5005 and the CCU 5039 is performed by wireless communication, there is no necessity to lay the transmission cable 5065 in the operating room. Therefore, such a situation that movement of medical staff in the operating room is disturbed by the transmission cable 5065 can be eliminated.

An example of the endoscopic surgery system 5000 to which the technology according to the present disclosure can be applied has been described above. It is to be noted here that, although the endoscopic surgery system 5000 has been described as an example, the system to which the technology according to the present disclosure can be applied is not limited to the example. For example, the technology according to the present disclosure may be applied to a flexible endoscopic system for inspection or a microscopic surgery system.

The image sensor module according to the present technology is favorably applicable to the endoscope 5001 among the above-described structural elements. In the medical fields, a sterilization process called autoclave treatment is necessary for medical instruments such as surgical instruments. In the autoclave treatment, the sterilization process is performed in saturated steam at a temperature of 100° C. to 150° C., for example. Therefore, the endoscope 5001 gets thermal shock due to temperature cycling. As described above, when using the image sensor module according to the present technology, it is possible to absorb and alleviate thermal stress and thermal strain that occur due to difference in coefficients of thermal expansion between the substrate 10 and the image sensor 20. Therefore, it is possible to ensure long-term reliability of products of the endoscope 5001 including the image sensor module.

6.2) Second Application Example

Next, another example of the endoscopic surgery system will be described. The image sensor module including the MID according to each of the above-described embodiments is also applicable to an endoscope of an endoscopic surgery system described below.

Figure 22:
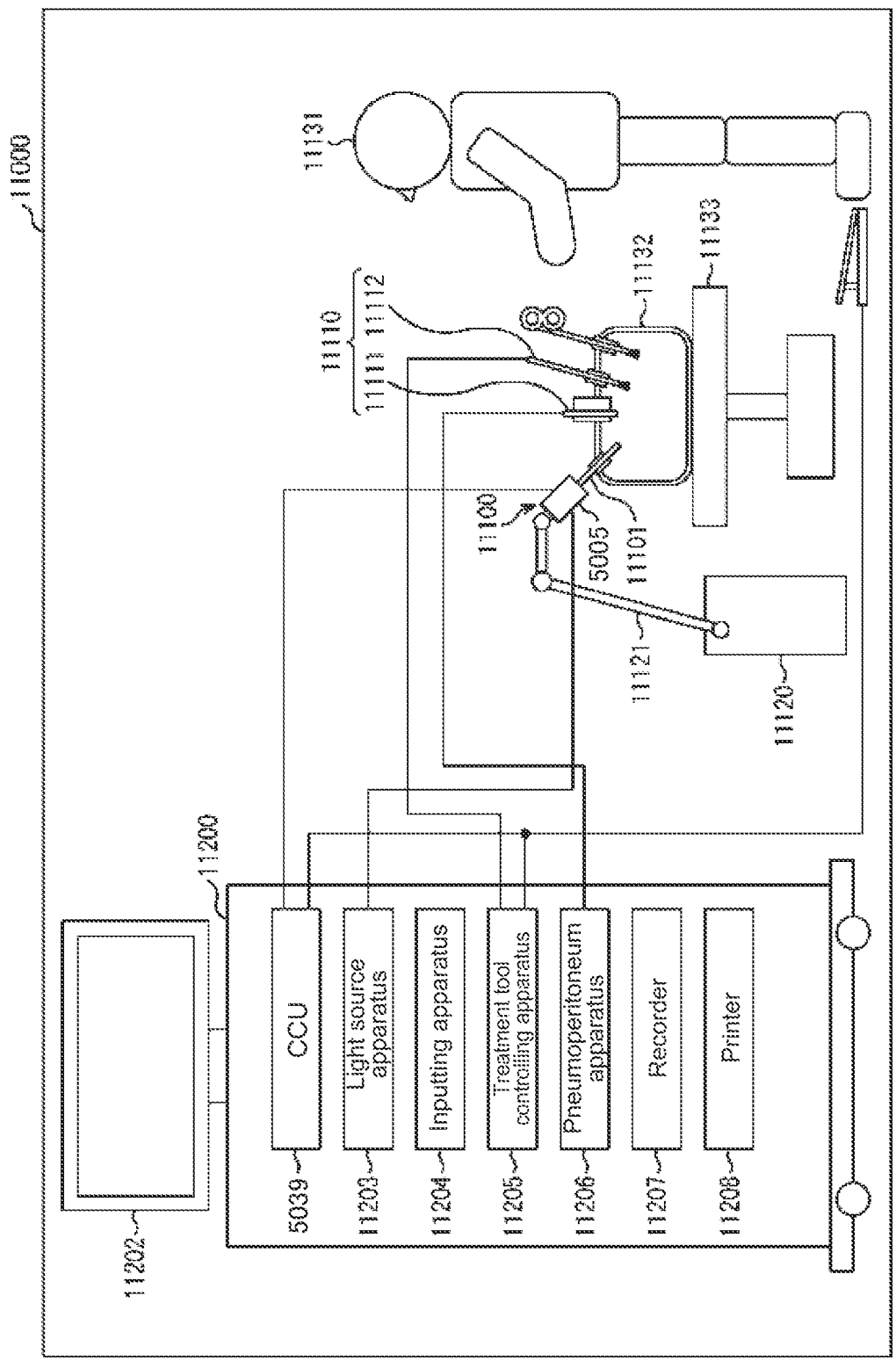
FIG. 22 is a diagram illustrating another example of a schematic configuration of an endoscopic surgery system.

FIG. 22 is a diagram illustrating an example of a schematic configuration of an endoscopic surgery system to which the technology according to the present disclosure (the present technology) can be applied.

In FIG. 22, a state is illustrated in which a surgeon (medical doctor) 11131 is using an endoscopic surgery system 11000 to perform surgery for a patient 11132 on a patient bed 11133. As depicted, the endoscopic surgery system 11000 includes an endoscope 11100, other surgical tools 11110 such as a pneumoperitoneum tube 11111 and an energy device 11112, a supporting arm apparatus 11120 which supports the endoscope 11100 thereon, and a cart 11200 on which various apparatus for endoscopic surgery are mounted.

The endoscope 11100 includes a lens barrel 11101 which has a region of a predetermined length from a distal end thereof to be inserted into a body cavity of the patient 11132, and a camera head 5005 connected to a proximal end of the lens barrel 11101. In the example depicted, the endoscope 11100 is depicted as a so-called rigid endoscope having the lens barrel 11101 of the hard type. However, the endoscope 11100 may otherwise be configured as a so-called flexible endoscope having the lens barrel of the flexible type.

The lens barrel 11101 has, at a distal end thereof, an opening in which an objective lens is fitted. A light source apparatus 11203 is connected to the endoscope 11100 such that light generated by the light source apparatus 11203 is introduced to the distal end of the lens barrel by a light guide extending in the inside of the lens barrel 11101 and is radiated toward an observation target in a body cavity of the patient 11132 through the objective lens. It is to be noted that the endoscope 11100 may be a forward-viewing endoscope or may be an oblique-viewing endoscope or a side-viewing endoscope.

An optical system and an image pickup element are provided in the inside of the camera head 5005 such that reflected light (observation light) from an observation target is condensed on the image pickup element by the optical system. The observation light is photoelectrically converted by the image pickup element to generate an electric signal corresponding to the observation light, namely, an image signal corresponding to an observation image. The image signal is transmitted as RAW data to a camera control unit (CCU) 11201.

The CCU 5039 includes a central processing unit (CPU), a graphics processing unit (GPU) or the like and integrally controls operation of the endoscope 11100 and a display apparatus 11202. Further, the CCU 5039 receives an image signal from the camera head 5005 and performs, for the image signal, various image processes for displaying an image based on the image signal such as, for example, a development process (demosaic process).

The display apparatus 11202 displays an image based on an image signal for which the image processes have been performed by the CCU 5039 under the control of the CCU 5039.

The light source apparatus 11203 includes a light source such as, for example, a light emitting diode (LED) and supplies irradiation light for imaging of a surgical region or the like to the endoscope 11100.

An inputting apparatus 11204 is an input interface for the endoscopic surgery system 11000. A user can input various kinds of information or instructions to the endoscopic surgery system 11000 through the inputting apparatus 11204. For example, the user would input an instruction or a like to change an image pickup condition (type of irradiation light, magnification, focal length or the like) of the endoscope 11100.

A treatment tool controlling apparatus 11205 controls driving of the energy device 11112 for cautery or incision of a tissue, sealing of a blood vessel or the like. A pneumoperitoneum apparatus 11206 feeds gas into a body cavity of the patient 11132 through the pneumoperitoneum tube 11111 to inflate the body cavity in order to secure the field of view of the endoscope 11100 and secure the working space for the surgeon. A recorder 11207 is an apparatus capable of recording various kinds of information relating to surgery. A printer 11208 is an apparatus capable of printing various kinds of information relating to surgery in various forms such as a text, an image or a graph.

It is to be noted that the light source apparatus 11203 which supplies irradiation light for imaging a surgical region to the endoscope 11100 may include a white light source which includes, for example, an LED, a laser light source or a combination of them. Where the white light source includes a combination of RGB laser light sources, since the output intensity and the output timing can be controlled with a high degree of accuracy for each color (each wavelength), adjustment of the white balance of a captured image can be performed by the light source apparatus 11203. Further, in this case, if laser light beams from the respective RGB laser light sources are radiated time-divisionally on an observation target and driving of the image pickup element of the camera head 5005 is controlled in synchronism with the radiation timings, then images individually corresponding to the R, G and B colors can be captured time-divisionally. According to the method just described, a color image can be obtained even if a color filter is not provided for the image pickup element.

Further, driving of the light source apparatus 11203 may be controlled such that the intensity of light to be output is changed for each predetermined time. By controlling driving of the image pickup element of the camera head 5005 in synchronism with the timing of the change of the intensity of light to acquire images time-divisionally and synthesizing the images, an image of a high dynamic range free from so-called blocked-up shadows and blown-out highlights can be created.

Further, the light source apparatus 11203 may be configured to supply light of a predetermined wavelength band ready for special light observation. In the special light observation, for example, by utilizing the wavelength dependency of absorption of light in a body tissue to radiate light of a narrower wavelength band in comparison with irradiation light utilized upon ordinary observation (namely, white light), so-called narrow band light observation (narrow band imaging) of imaging a predetermined tissue such as a blood vessel of a superficial portion of the mucous membrane or the like in a high contrast is performed. Alternatively, in the special light observation, fluorescent observation for obtaining an image from fluorescent light generated by radiation of excitation light may be performed. In the fluorescent observation, it is possible to perform observation of fluorescent light from a body tissue by radiating excitation light on the body tissue (autofluorescence observation), to obtain a fluorescent light image by locally injecting a reagent such as indocyanine green (ICG) into a body tissue and radiating excitation light corresponding to a fluorescent light wavelength of the reagent on the body tissue, or the like. The light source apparatus 11203 can be configured to supply such narrow-band light and/or excitation light suitable for the special light observation as described above.

FIG. 21 is a block diagram depicting an example of a functional configuration of the camera head 5005 and the CCU 5039 depicted in FIG. 22.

The camera head 5005 includes a lens unit 5007, an image pickup unit 5009, a driving unit 5011, a communication unit 5013 and a camera head controlling unit 5015. The CCU 5039 includes a communication unit 5059, an image processing unit 5061 and a control unit 5063. The camera head 5005 and the CCU 5039 are connected to be communicable by a transmission cable 11400.

The lens unit 5007 is an optical system provided at a connecting location of the camera head 5005 to the lens barrel 11101. Observation light taken in from the distal end of the lens barrel 11101 is introduced into the camera head 5005 and enters the lens unit 5007. The lens unit 5007 includes a combination of a plurality of lenses including a zoom lens and a focusing lens.

The number of image pickup elements which is included by the image pickup unit 5009 may be one (single-plate type) or a plural number (multi-plate type). Where the image pickup unit 5009 is configured as an image pickup unit of the multi-plate type, for example, image signals corresponding to respective R, G and B are generated by the image pickup elements, and the image signals may be synthesized to obtain a color image. Alternatively, the image pickup unit 5009 may also be configured so as to have a pair of image pickup elements for acquiring respective image signals for the right eye and the left eye compatible with three dimensional (3D) display. Where 3D display is applied, the surgeon 11131 can comprehend the depth of a living body tissue in the surgical region more accurately. It is to be noted that, if the image pickup unit 5009 is configured as an image pickup unit of the multi-plate type, then a plurality of systems of lens units 5007 is provided in a manner that the systems correspond to the respective image pickup elements.

In addition, the image pickup unit 5009 may not necessarily be provided on the camera head 5005. For example, the image pickup unit 5009 may be provided just behind the objective lens in the inside of the lens barrel 11101.

The driving unit 5011 includes an actuator and moves the zoom lens and the focusing lens of the lens unit 5007 by a predetermined distance along the optical axis under the control of the camera head controlling unit 5015. Consequently, the magnification and the focal point of an image to be captured by the image pickup unit 5009 can be adjusted suitably.

The communication unit 5013 includes a communication apparatus for transmitting and receiving various kinds of information to and from the CCU 5039. The communication unit 5013 transmits an image signal acquired from the image pickup unit 5009 as RAW data to the CCU 5039 through the transmission cable 11400.

In addition, the communication unit 5013 receives a control signal for controlling driving of the camera head 5005 from the CCU 5039 and supplies the control signal to the camera head controlling unit 5015. The control signal includes information relating to image pickup conditions such as, for example, information that a frame rate of an image to be captured is designated, information that an exposure value of image capturing is designated, and/or information that a magnification and a focal point of an image to be captured are designated.

It is to be noted that the image pickup conditions such as the frame rate, exposure value, magnification and focal point may be suitably designated by the user or may be set automatically by the control unit 5063 of the CCU 5039 on the basis of an acquired image signal. In the latter case, a so-called auto exposure (AE) function, an auto focus (AF) function and an auto white balance (AWB) function are incorporated in the endoscope 11100.

The camera head controlling unit 5015 controls driving of the camera head 5005 on the basis of a control signal received from the CCU 5039 through the communication unit 5013.

The communication unit 5059 includes a communication apparatus for transmitting and receiving various kinds of information to and from the camera head 5005. The communication unit 5059 receives an image signal transmitted thereto from the camera head 5005 through the transmission cable 11400.

Further, the communication unit 5059 transmits, to the camera head 5005, a control signal for controlling driving of the camera head 5005. The image signal and the control signal can be transmitted by electrical communication, optical communication, or the like.

The image processing unit 5061 performs various image processes for an image signal in the form of RAW data transmitted thereto from the camera head 5005.

The control unit 5063 performs various kinds of control relating to image capturing of a surgical region or the like by the endoscope 11100 and display of a captured image obtained by capturing of an image of the surgical region or the like. For example, the control unit 5063 generates a control signal for controlling driving of the camera head 5005.

Further, the control unit 5063 controls, on the basis of an image signal for which the image process has been performed by the image processing unit 5061, the display apparatus 11202 to display a captured image that shows the surgical region or the like. Thereupon, the control unit 5063 may recognize various objects in the captured image using various image recognition technologies. For example, the control unit 5063 can recognize a surgical tool such as forceps, a particular living body region, bleeding, mist appeared when the energy device 11112 is used and so forth by detecting the shape, color and so forth of edges of the objects included in the captured image. The control unit 5063 may cause, when it controls the display apparatus 11202 to display a captured image, various kinds of surgery supporting information to be displayed in an overlapping manner with an image of the surgical region using a result of the recognition. Where the surgery supporting information is displayed in an overlapping manner and presented to the surgeon 11131, the burden on the surgeon 11131 can be reduced and the surgeon 11131 can proceed with the surgery with certainty.

The transmission cable 11400 which connects the camera head 5005 and the CCU 5039 to each other is an electric signal cable ready for communication of an electric signal, an optical fiber ready for optical communication, or a composite cable ready for both of electrical communication and optical communication.

Here, while, in the example depicted, communication is performed by wired communication using the transmission cable 11400, the communication between the camera head 5005 and the CCU 5039 may be performed otherwise by wireless communication.

6.3) Third Application Example

The technology according to the present disclosure may be applied to a mobile camera that is installed in a mobile object. Examples of the mobile object includes vehicles, electric vehicles, hybrid electric vehicles, motorcycles, bicycles, personal transporters, airplanes, drones, ships, robots, heavy equipment, agricultural machinery (tractors), and the like, for example.

Figure 23:
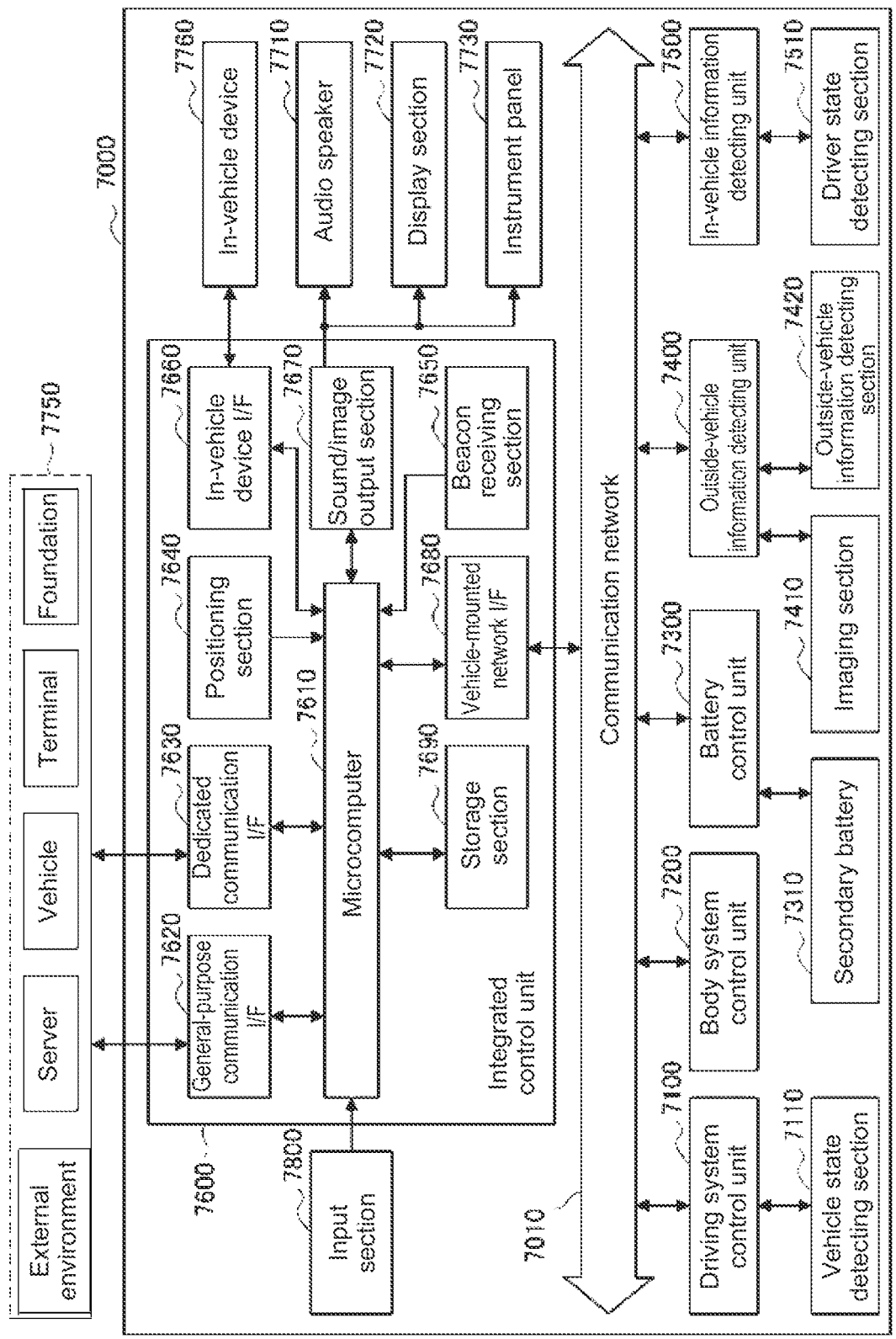
FIG. 23 is a block diagram illustrating an example of a schematic configuration of a vehicle control system.

FIG. 23 is a block diagram depicting a schematic configuration example of a vehicle control system 7000 as an example of a mobile object control system to which the technology according to the present disclosure can be applied. The vehicle control system 7000 includes a plurality of electronic control units connected to each other via a communication network 7010. In the example depicted in FIG. 23, the vehicle control system 7000 includes a driving system control unit 7100, a body system control unit 7200, a battery control unit 7300, an outside-vehicle information detecting unit 7400, an in-vehicle information detecting unit 7500, and an integrated control unit 7600. The communication network 7010 connecting the plurality of control units to each other may, for example, be a vehicle-mounted communication network compliant with any standard such as controller area network (CAN), local interconnect network (LIN), local area network (LAN), FlexRay (registered trademark), or the like.

Each of the control units includes: a microcomputer that performs arithmetic processing according to various kinds of programs; a storage section that stores the programs executed by the microcomputer, parameters used for various kinds of arithmetic operations, or the like; and a driving circuit that drives various kinds of control target devices. Each of the control units further includes: a network I/F for performing communication with other control units via the communication network 7010; and a communication I/F for performing communication with a device, a sensor, or the like within and without the vehicle by wired communication or wireless communication. AS functional configurations of the integrated control unit 7600, FIG. 23 illustrates a microcomputer 7610, a general-purpose communication I/F 7620, a dedicated communication I/F 7630, a positioning section 7640, a beacon receiving section 7650, an in-vehicle device I/F 7660, a sound/image output section 7670, a vehicle-mounted network I/F 7680, and a storage section 7690. The other control units similarly include a microcomputer, a communication I/F, a storage section, and the like.

The driving system control unit 7100 controls operation of devices related to the driving system of the vehicle in accordance with various kinds of programs. For example, the driving system control unit 7100 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like. The driving system control unit 7100 may have a function of a control device such as an antilock brake system (ABS), electronic stability control (ESC), or the like.

The driving system control unit 7100 is connected with a vehicle state detecting section 7110. The vehicle state detecting section 7110, for example, includes at least one of a gyro sensor that detects the angular velocity of axial rotational movement of a vehicle body, an acceleration sensor that detects the acceleration of the vehicle, or sensors for detecting an amount of operation of an accelerator pedal, an amount of operation of a brake pedal, the steering angle of a steering wheel, the number of revolutions of an engine, rotational speeds of wheels, and the like. The driving system control unit 7100 performs arithmetic processing using a signal input from the vehicle state detecting section 7110, and controls the internal combustion engine, the driving motor, an electric power steering device, the brake device, and the like.

The body system control unit 7200 controls the operation of various kinds of devices provided to the vehicle body in accordance with various kinds of programs. For example, the body system control unit 7200 functions as a control device for a keyless entry system, a smart key system, a power window device, or various kinds of lamps such as headlamps, tail lamps, brake lamps, turn signals, fog lamps, and the like. In this case, radio waves transmitted from a mobile device serving as an alternative to a key or signals of various kinds of switches can be input to the body system control unit 7200. The body system control unit 7200 receives these input radio waves or signals, and controls a door lock device, the power window device, the lamps, or the like of the vehicle.

The battery control unit 7300 controls a secondary battery 7310, which is a power supply source for the driving motor, in accordance with various kinds of programs. For example, the battery control unit 7300 is supplied with information about a battery temperature, a battery output voltage, an amount of charge remaining in the battery, or the like from a battery device including the secondary battery 7310. The battery control unit 7300 performs arithmetic processing using these signals, and performs control for regulating the temperature of the secondary battery 7310 or controls a cooling device provided to the battery device or the like.

The outside-vehicle information detecting unit 7400 detects information about the outside of the vehicle including the vehicle control system 7000. For example, the outside-vehicle information detecting unit 7400 is connected with at least one of an imaging section 7410 or an outside-vehicle information detecting section 7420. The imaging section 7410 includes at least one of a time-of-flight (ToF) camera, a stereo camera, a monocular camera, an infrared camera, or other cameras. The outside-vehicle information detecting section 7420, for example, includes at least one of an environmental sensor for detecting current atmospheric conditions or weather conditions or a peripheral information detecting sensor for detecting another vehicle, an obstacle, a pedestrian, or the like on the periphery of the vehicle including the vehicle control system 7000.

The environmental sensor, for example, may be at least one of a rain drop sensor for detecting rain, a fog sensor for detecting a fog, a sunshine sensor for detecting a degree of sunshine, or a snow sensor for detecting snowfall. The peripheral information detecting sensor may be at least one of an ultrasonic sensor, a radar device, or a Lidar (light detection and ranging, or light imaging, detection, and ranging) device. Each of the imaging section 7410 and the outside-vehicle information detecting section 7420 may be provided as an independent sensor or device, or may be provided as a device in which a plurality of sensors or devices is integrated.

Figure 24:
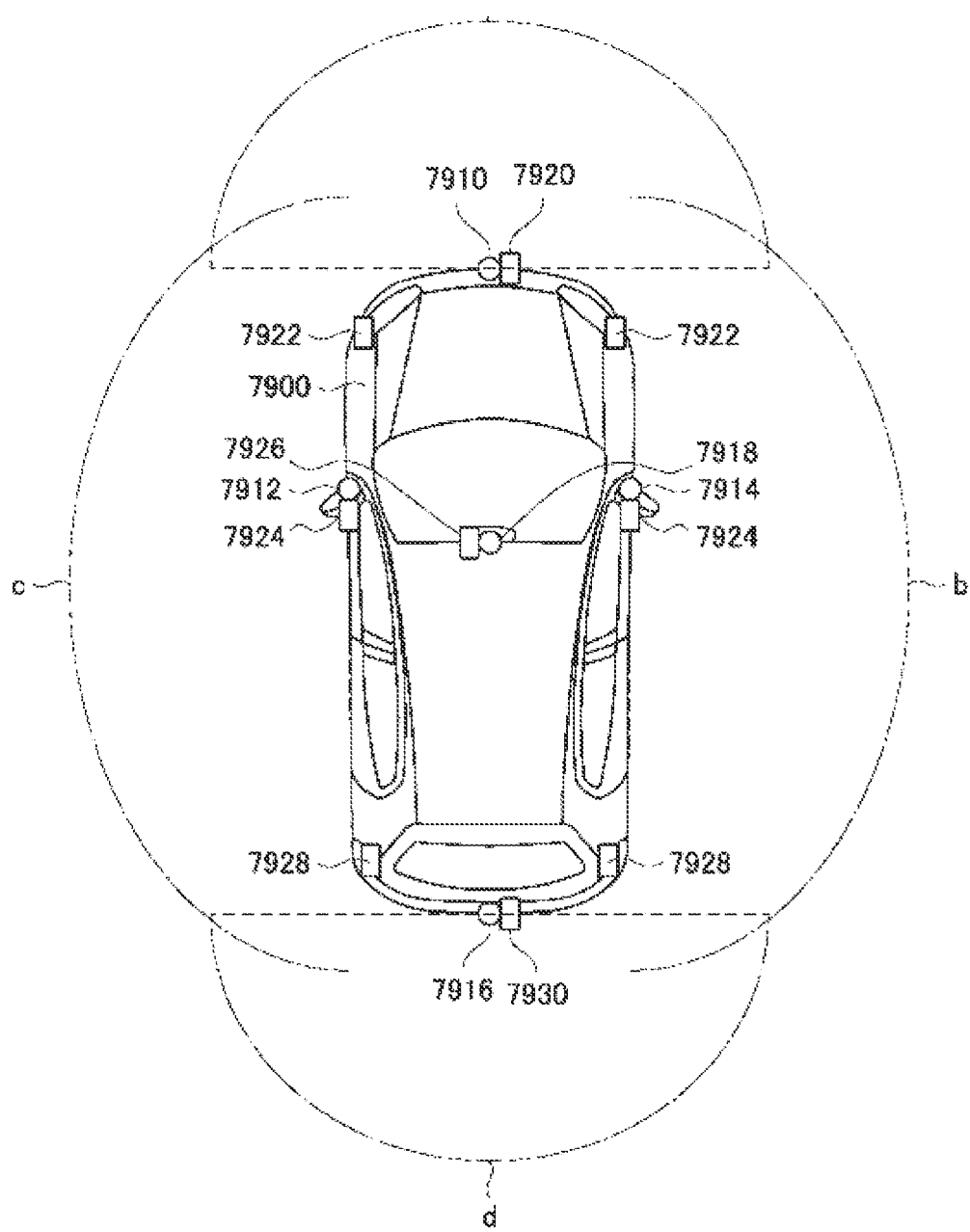
FIG. 24 is an explanatory diagram illustrating an example of installation positions of an outside-vehicle information detecting section and an imaging section.

Here, FIG. 24 depicts an example of installation positions of the imaging section 7410 and the outside-vehicle information detecting section 7420. Imaging sections 7910, 7912, 7914, 7916, and 7918 are, for example, disposed at at least one of positions on a front nose, sideview mirrors, a rear bumper, a back door, or an upper portion of a windshield within the interior of the vehicle 7900. The imaging section 7910 provided to the front nose and the imaging section 7918 provided to the upper portion of the windshield within the interior of the vehicle mainly obtain images of the front of the vehicle 7900. The imaging sections 7912 and 7914 provided to the sideview mirrors mainly obtain images of the sides of the vehicle 7900. The imaging section 7916 provided to the rear bumper or the back door mainly obtains an image of the rear of the vehicle 7900. The imaging section 7918 provided to the upper portion of the windshield within the interior of the vehicle is used mainly to detect a preceding vehicle, a pedestrian, an obstacle, a traffic light, a traffic sign, a lane, or the like.

Incidentally, FIG. 24 depicts an example of photographing ranges of the respective imaging sections 7910, 7912, 7914, and 7916. An imaging range a represents the imaging range of the imaging section 7910 provided to the front nose. Imaging ranges b and c respectively represent the imaging ranges of the imaging sections 7914 and 7912 provided to the sideview mirrors. An imaging range d represents the imaging range of the imaging section 7916 provided to the rear bumper or the back door. A bird's-eye image of the vehicle 7900 as viewed from above can be obtained by superimposing image data captured by the imaging sections 7910, 7912, 7914, and 7916, for example.

Outside-vehicle information detecting sections 7920, 7922, 7924, 7926, 7928, and 7930 provided to the front, rear, sides, corners, and the upper portion of the windshield within the interior of the vehicle 7900 may be, for example, ultrasonic sensors or radar devices. The outside-vehicle information detecting sections 7920, 7926, and 7930 provided to the front nose, the rear bumper or the back door, and the upper portion of the windshield within the interior of the vehicle 7900 may be Lidar devices, for example. These outside-vehicle information detecting sections 7920 to 7930 are used mainly to detect a preceding vehicle, a pedestrian, an obstacle, or the like.

Returning to FIG. 23, the description will be continued. The outside-vehicle information detecting unit 7400 causes the imaging section 7410 to capture an image of an outside of the vehicle, and receives captured image data. In addition, the outside-vehicle information detecting unit 7400 receives detection information from the outside-vehicle information detecting section 7420 connected to the outside-vehicle information detecting unit 7400. In a case where the outside-vehicle information detecting section 7420 is the ultrasonic sensor, the radar device, or the Lidar device, the outside-vehicle information detecting unit 7400 causes transmission of an ultrasonic wave, an electromagnetic wave, or the like, and receives information of a received reflected wave. On the basis of the received information, the outside-vehicle information detecting unit 7400 may perform processing of detecting an object such as a human, a vehicle, an obstacle, a sign, a character on a road surface, or the like, or processing of detecting a distance thereto. The outside-vehicle information detecting unit 7400 may perform environment recognition processing of recognizing rainfall, a fog, road surface conditions, or the like on the basis of the received information. The outside-vehicle information detecting unit 7400 may calculate a distance to an object outside the vehicle on the basis of the received information.

In addition, on the basis of the received image data, the outside-vehicle information detecting unit 7400 may perform image recognition processing of recognizing a human, a vehicle, an obstacle, a sign, a character on a road surface, or the like, or processing of detecting a distance thereto. The outside-vehicle information detecting unit 7400 may subject the received image data to processing such as distortion correction, alignment, or the like, and combine the image data captured by different imaging sections 7410 to generate a bird's-eye image or a panoramic image. The outside-vehicle information detecting unit 7400 may perform view-point conversion processing using the image data captured by the different imaging sections 7410.

The in-vehicle information detecting unit 7500 detects information about the inside of the vehicle. The in-vehicle information detecting unit 7500 is, for example, connected with a driver state detecting section 7510 that detects the state of a driver. The driver state detecting section 7510 may include a camera that images the driver, a biosensor that detects biological information of the driver, a microphone that collects sound within the interior of the vehicle, or the like. The biosensor is, for example, disposed on a seat surface, the steering wheel, or the like, and detects biological information of an occupant sitting in a seat or the driver holding the steering wheel. On the basis of detection information input from the driver state detecting section 7510, the in-vehicle information detecting unit 7500 may calculate a degree of fatigue of the driver or a degree of concentration of the driver, or may determine whether the driver is dozing. The in-vehicle information detecting unit 7500 may subject an audio signal obtained by the collection of the sound to processing such as noise canceling processing or the like.

The integrated control unit 7600 controls general operation within the vehicle control system 7000 in accordance with various kinds of programs. The integrated control unit 7600 is connected with an input section 7800. The input section 7800 is implemented by a device capable that may be operated by an occupant through input operation, such, for example, as a touchscreen, a button, a microphone, a switch, a lever, or the like. The integrated control unit 7600 may be supplied with data obtained by voice recognition of voice input through the microphone. The input section 7800 may, for example, be a remote control device using infrared rays or other radio waves, or an external connecting device such as a mobile telephone, a personal digital assistant (PDA), or the like that supports operation of the vehicle control system 7000. The input section 7800 may be, for example, a camera. In that case, an occupant can input information by gesture. Alternatively, data may be input which is obtained by detecting the movement of a wearable device that the occupant wears. Further, the input section 7800 may, for example, include an input control circuit or the like that generates an input signal on the basis of information input by an occupant or the like using the above-described input section 7800, and that outputs the generated input signal to the integrated control unit 7600. The occupant or the like inputs various kinds of data or gives an instruction for processing operation to the vehicle control system 7000 by operating the input section 7800.

The storage section 7690 may include a read only memory (ROM) that stores various kinds of programs executed by the microcomputer and a random access memory (RAM) that stores various kinds of parameters, arithmetic operation results, sensor values, or the like. In addition, the storage section 7690 may be implemented by a magnetic storage device such as a hard disc drive (HDD), a semiconductor storage device, an optical storage device, a magneto-optical storage device, or the like.

The general-purpose communication I/F 7620 is a general-purpose communication I/F, which mediates communication with various apparatuses present in an external environment 7750. The general-purpose communication I/F 7620 may implement a cellular communication protocol such as Global System for Mobile Communications (GSM) (registered trademark), WiMAX (registered trademark), Long-Term Evolution (LTE) (registered trademark), LTE advanced (LTE-A), or the like, or another wireless communication protocol such Bluetooth or the like. The general-purpose communication I/F 7620 may, for example, connect to an apparatus (for example, an application server or a control server) present on an external network (for example, the Internet, a cloud network, or a company-specific network) via a base station or an access point. In addition, the general-purpose communication I/F 7620 may connect to a terminal present in the vicinity of the vehicle (for example, a terminal of the driver, a pedestrian, or a store, or a machine type communication (MTC) terminal) using a peer-to-peer (P2P) technology, for example.

The dedicated communication I/F 7630 is a communication I/F that supports a communication protocol developed for use in vehicles. The dedicated communication I/F 7630 may implement a standard protocol such, for example, as wireless access in vehicle environment (WAVE), which is a combination of IEEE 802.11p serving as a lower layer and IEEE 1609 serving as a higher layer, dedicated short range communications (DSRC), or a cellular communication protocol. The dedicated communication I/F 7630 typically carries out V2X communication as a concept including one or more of vehicle-to-vehicle communication, vehicle-to-infrastructure communication, vehicle-to-home communication, and vehicle-to-pedestrian communication.

The positioning section 7640, for example, performs positioning by receiving a Global Navigation Satellite System (GNSS) signal from a GNSS satellite (for example, a Global Positioning System (GPS) signal from a GPS satellite), and generates positional information including the latitude, longitude, and altitude of the vehicle. Incidentally, the positioning section 7640 may identify a current position by exchanging signals with a wireless access point, or may obtain positional information from a terminal such as a mobile phone, a PHS, or a smartphone that has a positioning function.

The beacon receiving section 7650, for example, receives a radio wave or an electromagnetic wave transmitted from a radio station installed on a road or the like, and thereby obtains information about the current position, traffic congestion, a closed road, a necessary time, or the like. Incidentally, the function of the beacon receiving section 7650 may be included in the dedicated communication I/F 7630 described above.

The in-vehicle device I/F 7660 is a communication interface that mediates connection between the microcomputer 7610 and various in-vehicle devices 7760 present within the vehicle. The in-vehicle device I/F 7660 may establish wireless connection using a wireless communication protocol such as a wireless LAN, Bluetooth (registered trademark), near-field communication (NFC), or wireless Universal Serial Bus (WUSB). In addition, the in-vehicle device I/F 7660 may establish wired connection by Universal Serial Bus (USB), High-Definition Multimedia Interface (HDMI (registered trademark)), Mobile High-Definition Link (MHL), or the like via a connection terminal (and a cable if necessary) that is not depicted in the drawings. The in-vehicle devices 7760 may, for example, include at least one of a mobile device possessed by an occupant, a wearable device, or an information device carried into or attached to the vehicle. In addition, the in-vehicle devices 7760 may also include a navigation device that searches for a path to any destination. The in-vehicle device I/F 7660 exchanges control signals or data signals with these in-vehicle devices 7760.

The vehicle-mounted network I/F 7680 is an interface that mediates communication between the microcomputer 7610 and the communication network 7010. The vehicle-mounted network I/F 7680 transmits and receives signals or the like in conformity with a predetermined protocol supported by the communication network 7010.

The microcomputer 7610 of the integrated control unit 7600 controls the vehicle control system 7000 in accordance with various kinds of programs on the basis of information obtained via at least one of the general-purpose communication I/F 7620, the dedicated communication I/F 7630, the positioning section 7640, the beacon receiving section 7650, the in-vehicle device I/F 7660, or the vehicle-mounted network I/F 7680. For example, the microcomputer 7610 may calculate a control target value for the driving force generating device, the steering mechanism, or the braking device on the basis of the obtained information about the inside and outside of the vehicle, and output a control command to the driving system control unit 7100. For example, the microcomputer 7610 may perform cooperative control intended to implement functions of an advanced driver-assistance system (ADAS) which include collision avoidance or shock mitigation for the vehicle, following driving based on a following distance, vehicle speed maintaining driving, warning of collision of the vehicle, warning of deviation of the vehicle from a lane, or the like. In addition, the microcomputer 7610 may perform cooperative control intended for autocruise, which allows the vehicle to travel autonomously without depending on the operation performed by the driver, or the like, by controlling the driving force generating device, the steering mechanism, the braking device, or the like on the basis of the obtained information about the surroundings of the vehicle.

The microcomputer 7610 may generate three-dimensional distance information between the vehicle and an object such as a structure, a person, or the like near the vehicle, and generate local map information including information about the surroundings of the current position of the vehicle, on the basis of information obtained via at least one of the general-purpose communication I/F 7620, the dedicated communication I/F 7630, the positioning section 7640, the beacon receiving section 7650, the in-vehicle device I/F 7660, or the vehicle-mounted network I/F 7680. In addition, the microcomputer 7610 may predict danger such as collision of the vehicle, approaching of a pedestrian or the like, entry to a closed road, or the like on the basis of the obtained information, and generate a warning signal. The warning signal may, for example, be a signal for producing a warning sound or lighting a warning lamp.

The sound/image output section 7670 transmits an output signal of at least one of a sound or an image to an output device capable of visually or auditorily notifying information to an occupant of the vehicle or to the outside of the vehicle. In the example of FIG. 23, an audio speaker 7710, a display section 7720, and an instrument panel 7730 are illustrated as the output device. The display section 7720 may, for example, include at least one of an on-board display or a head-up display. The display section 7720 may have an augmented reality (AR) display function. The output device may be other than these devices, and may be another device such as headphones, a wearable device such as an eyeglass type display worn by an occupant or the like, a projector, a lamp, or the like. In a case where the output device is a display device, the display device visually displays results obtained by various kinds of processing performed by the microcomputer 7610 or information received from another control unit in various forms such as text, an image, a table, a graph, or the like. In addition, in a case where the output device is an audio output device, the audio output device converts an audio signal including reproduced audio data, sound data, or the like into an analog signal, and auditorily outputs the analog signal.

Incidentally, at least two control units connected to each other via the communication network 7010 in the example depicted in FIG. 23 may be integrated into one control unit. Alternatively, each individual control unit may include a plurality of control units. Further, the vehicle control system 7000 may include another control unit not depicted in the drawings. In addition, part or the whole of the above-described functions performed by any of the control units may be assigned to another control unit. That is, predetermined arithmetic processing may be performed by any of the control units as long as information is transmitted and received via the communication network 7010. Similarly, a sensor or a device connected to any of the control units may be connected to another control unit, and a plurality of control units may mutually transmit and receive detection information via the communication network 7010.

The camera that includes the image sensor module including the MID according to each of the above-described embodiments is applicable to the imaging section 7410, the driver state detecting section 7510, and the input section 7800 in the above-described vehicle control system 7000 according to the application example illustrated in FIG. 23. It is highly possible that the mobile object is exposed to both a high-temperature environment and a low-temperature environment. In the hot sun, the temperature of the inside of the vehicle may become 70° C. or more. When using the image sensor module according to the present technology, it is possible to absorb and alleviate thermal stress and thermal strain that occur due to difference in coefficients of thermal expansion between the substrate 10 and the image sensor 20. Therefore, it is possible to ensure long-term reliability of camera products including the image sensor modules.

6.4) Fourth Application Example

Next, another example of the vehicle control system will be described. The image sensor module including the MID according to the present technology is also applicable to a camera of a vehicle control system to be described below.

Figure 25:
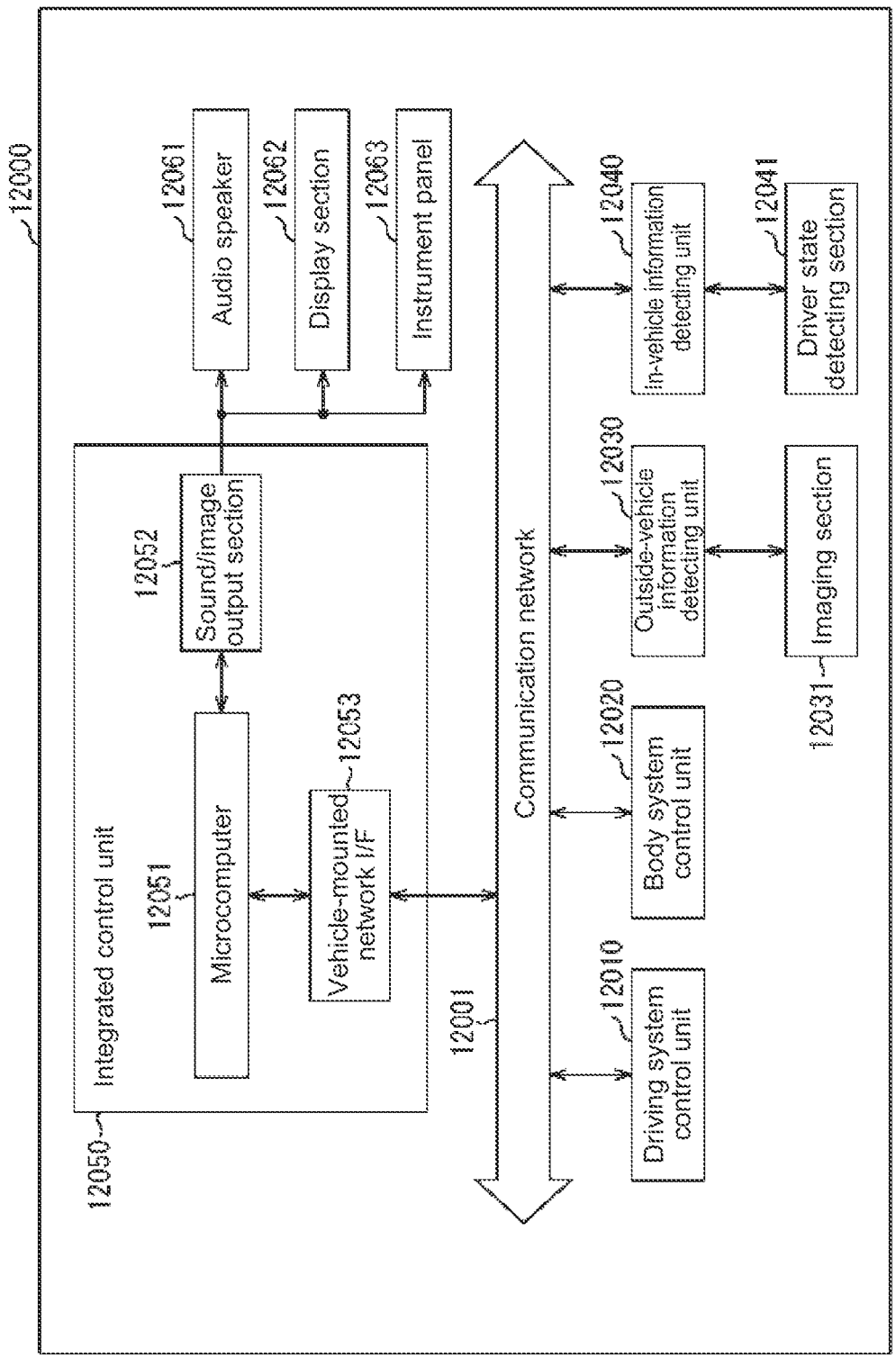
FIG. 25 is a block diagram illustrating another example of a schematic configuration of a vehicle control system.

FIG. 25 is a block diagram depicting a schematic configuration example of a vehicle control system as an example of a mobile body control system to which the technology according to the present disclosure can be applied.

The vehicle control system 12000 includes a plurality of electronic control units connected to each other via a communication network 12001. In the example depicted in FIG. 25, the vehicle control system 12000 includes a driving system control unit 12010, a body system control unit 12020, an outside-vehicle information detecting unit 12030, an in-vehicle information detecting unit 12040, and an integrated control unit 12050. In addition, a microcomputer 12051, a sound/image output section 12052, and a vehicle-mounted network interface (I/F) 12053 are illustrated as functional configurations of the integrated control unit 12050.

The driving system control unit 12010 controls the operation of devices related to the driving system of the vehicle in accordance with various kinds of programs. For example, the driving system control unit 12010 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like.

The body system control unit 12020 controls the operation of various kinds of devices provided to the vehicle body in accordance with various kinds of programs. For example, the body system control unit 12020 functions as a control device for a keyless entry system, a smart key system, a power window device, or various kinds of lamps such as headlamps, tail lamps, brake lamps, turn signals, fog lamps, and the like. In this case, radio waves transmitted from a mobile device serving as an alternative to a key or signals of various kinds of switches can be input to the body system control unit 12020. The body system control unit 12020 receives these input radio waves or signals, and controls a door lock device, the power window device, the lamps, or the like of the vehicle.

The outside-vehicle information detecting unit 12030 detects information about the outside of the vehicle including the vehicle control system 12000. For example, the outside-vehicle information detecting unit 12030 is connected with an imaging section 12031. The outside-vehicle information detecting unit 12030 causes the imaging section 12031 to capture an image of the outside of the vehicle, and receives the captured image. On the basis of the received image, the outside-vehicle information detecting unit 12030 may perform processing of detecting an object such as a human, a vehicle, an obstacle, a sign, a character on a road surface, or the like, or processing of detecting a distance thereto.

The imaging section 12031 is an optical sensor that receives light, and that outputs an electric signal corresponding to a received light amount of the light. The imaging section 12031 can output the electric signal as an image, or can output the electric signal as ranging information. In addition, the light received by the imaging section 12031 may be visible light, or may be invisible light such as infrared rays or the like.

The in-vehicle information detecting unit 12040 detects information about the inside of the vehicle. The in-vehicle information detecting unit 12040 is, for example, connected with a driver state detecting section 12041 that detects the state of a driver. The driver state detecting section 12041, for example, includes a camera that images the driver. On the basis of detection information input from the driver state detecting section 12041, the in-vehicle information detecting unit 12040 may calculate a degree of fatigue of the driver or a degree of concentration of the driver, or may determine whether the driver is dozing.

The microcomputer 12051 can calculate a control target value for the driving force generating device, the steering mechanism, or the braking device on the basis of the information about the inside or outside of the vehicle obtained by the outside-vehicle information detecting unit 12030 or the in-vehicle information detecting unit 12040, and output a control command to the driving system control unit 12010. For example, the microcomputer 12051 can perform cooperative control intended to implement functions of an advanced driver-assistance system (ADAS) which include collision avoidance or shock mitigation for the vehicle, following driving based on a following distance, vehicle speed maintaining driving, warning of collision of the vehicle, warning of deviation of the vehicle from a lane, or the like.

In addition, the microcomputer 12051 can perform cooperative control intended for autocruise, which allows the vehicle to travel autonomously without depending on the operation performed by the driver, or the like, by controlling the driving force generating device, the steering mechanism, the braking device, or the like on the basis of the information about the surroundings of the vehicle obtained by the outside-vehicle information detecting unit 12030 or the in-vehicle information detecting unit 12040.

In addition, the microcomputer 12051 can output a control command to the body system control unit 12030 on the basis of the information about the outside of the vehicle obtained by the outside-vehicle information detecting unit 12030. For example, the microcomputer 12051 can perform cooperative control intended to prevent glare by controlling the headlamps so as to change from a high beam to a low beam, for example, in accordance with the position of a preceding vehicle or an oncoming vehicle detected by the outside-vehicle information detecting unit 12030.

The sound/image output section 12052 transmits an output signal of at least one of a sound or an image to an output device capable of visually or auditorily notifying information to an occupant of the vehicle or to the outside of the vehicle. In the example of FIG. 25, an audio speaker 12061, a display section 12062, and an instrument panel 12063 are illustrated as the output device. The display section 12062 may, for example, include at least one of an on-board display or a head-up display.

Figure 26:
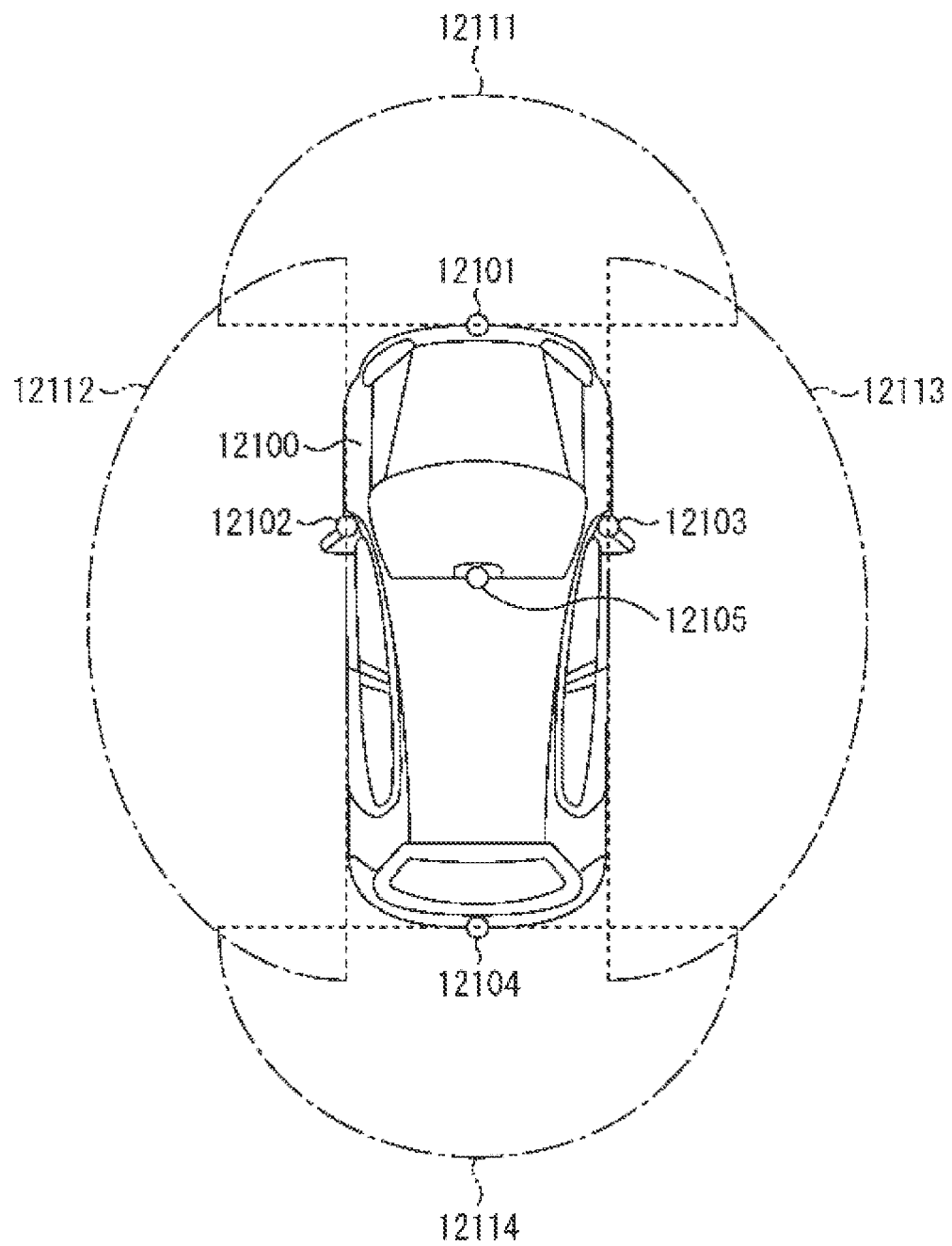
FIG. 26 is an explanatory diagram illustrating an example of installation positions of an outside-vehicle information detecting section and an imaging section.

FIG. 26 is a diagram depicting an example of the installation position of the imaging section 12031.

In FIG. 26, the imaging section 12031 includes imaging sections 12101, 12102, 12103, 12104, and 12105.

The imaging sections 12101, 12102, 12103, 12104, and 12105 are, for example, disposed at positions on a front nose, sideview mirrors, a rear bumper, and a back door, an upper portion of a windshield within the interior of the vehicle 12100. The imaging section 12101 provided to the front nose and the imaging section 12105 provided to the upper portion of the windshield within the interior of the vehicle mainly obtain images of the front of the vehicle 12100. The imaging sections 12102 and 12103 provided to the sideview mirrors mainly obtain images of the sides of the vehicle 12100. The imaging section 12104 provided to the rear bumper or the back door mainly obtains an image of the rear of the vehicle 12100. The imaging section 12105 provided to the upper portion of the windshield within the interior of the vehicle is used mainly to detect a preceding vehicle, a pedestrian, an obstacle, a traffic light, a traffic sign, a lane, or the like.

Incidentally, FIG. 26 depicts an example of photographing ranges of the imaging sections 12101 to 12104. An imaging range 12111 represents the imaging range of the imaging section 12101 provided to the front nose. Imaging ranges 12112 and 12113 respectively represent the imaging ranges of the imaging sections 12102 and 12103 provided to the sideview mirrors. An imaging range 12114 represents the imaging range of the imaging section 12104 provided to the rear bumper or the back door. A bird's-eye image of the vehicle 12100 as viewed from above is obtained by superimposing image data captured by the imaging sections 12101 to 12104, for example.

At least one of the imaging sections 12101 to 12104 may have a function of obtaining distance information. For example, at least one of the imaging sections 12101 to 12104 may be a stereo camera including a plurality of imaging elements, or may be an imaging element having pixels for phase difference detection.

For example, the microcomputer 12051 can determine a distance to each three-dimensional object within the imaging ranges 12111 to 12114 and a temporal change in the distance (relative speed with respect to the vehicle 12100) on the basis of the distance information obtained from the imaging sections 12101 to 12104, and thereby extract, as a preceding vehicle, a nearest three-dimensional object that is present on a traveling path of the vehicle 12100 in particular and that travels in substantially the same direction as the vehicle 12100 at a predetermined speed (for example, equal to or more than 0 km/hour). Further, the microcomputer 12051 can set a following distance to be maintained in front of a preceding vehicle in advance, and perform automatic brake control (including following stop control), automatic acceleration control (including following start control), or the like. It is thus possible to perform cooperative control intended for autocruise that allows the vehicle to travel autonomously without depending on the operation performed by the driver or the like.

For example, the microcomputer 12051 can classify pieces of three-dimensional object data related to three-dimensional objects into a two-wheeled vehicle, a standard-sized vehicle, a large-sized vehicle, a pedestrian, a utility pole, and other three-dimensional objects on the basis of the distance information obtained from the imaging sections 12101 to 12104, extract the classified three-dimensional object data, and use the extracted pieces of three-dimensional object data for automatic avoidance of obstacles. For example, the microcomputer 12051 identifies obstacles around the vehicle 12100 as obstacles that the driver of the vehicle 12100 can recognize visually and obstacles that are difficult for the driver of the vehicle 12100 to recognize visually. Then, the microcomputer 12051 determines a collision risk indicating a risk of collision with each obstacle. In a situation in which the collision risk is equal to or higher than a set value and there is thus a possibility of collision, the microcomputer 12051 outputs a warning to the driver via the audio speaker 12061 and the display section 12062, and performs forced deceleration or avoidance steering via the driving system control unit 12010. The microcomputer 12051 can thereby assist in driving to avoid collision.

At least one of the imaging sections 12101 to 12104 may be an infrared camera that detects infrared rays. The microcomputer 12051 can, for example, recognize a pedestrian by determining whether or not there is the pedestrian in images captured by the imaging sections 12101 to 12104. Such pedestrian recognition is, for example, performed by a procedure of extracting characteristic points in the images captured the imaging sections 12101 to 12104 serving as the infrared cameras and a procedure of determining whether or not it is the pedestrian by performing pattern matching processing on a series of the characteristic points representing the contour of an object. When the microcomputer 12051 determines that there is the pedestrian in the images captured by the imaging sections 12101 to 12104 and recognizes the pedestrian, the sound/image output section 12052 controls the display section 12062 so that the display section 12062 displays a square contour line superimposed on the recognized pedestrian for emphasis. In addition, the sound/image output section 12052 may also control the display section 12062 so that an icon or the like representing the pedestrian is displayed at a desired position.

Note that, the present technology may also be configured as below.

(1) An electronic component module including:
  a substrate that includes an electrode array;
  an electronic component that includes an electrode array; and
  a connection device that includes a plurality of post parts including respective conductive parts and a base for supporting the plurality of post parts, that is interposed between the substrate and the electronic component, and that is configured in a manner that the conductive parts electrically connect the electrode array of the substrate and the electrode array of the electronic component to each other via solder.

(2) The electronic component module according to (1), in which the connection device has a plurality of through holes in which the respective conductive parts are disposed.

(3) The electronic component module according to (2), in which axis centers of the through holes are disposed in a manner that the axis centers of the respective through holes are deviated from axis centers of the post parts.

(4) The electronic component module according to (2), in which axis centers of the respective through holes coincide with axis centers of the post parts.

(5) The electronic component module according to any one of (1) to (4), in which
  the base has a first surface that faces the substrate and a second surface that faces the electronic component, and
  the post parts include main bodies that protrude from at least one of the first surface or the second surface.

(6) The electronic component module according to (5), in which height of the main bodies from the first surface is different from height of the main bodies from the second surface.

(7) The electronic component module according to any one of (1) to (6), in which at least one of the post parts includes a step part that is formed like a step from the base, (8) The electronic component module according to any one of (1) to (7), in which main material of the connection device is resin.

(9) The electronic component module according to (8), in which a Young's modulus of the main material of the connection device is smaller than a Young's modulus of the solder.

(10) An endoscope that includes an image sensor module including:
  a substrate that includes an electrode array;
  an image sensor that includes an electrode array; and
  a connection device that includes a plurality of post parts including respective conductive parts and a base for supporting the plurality of post parts, that is interposed between the substrate and the image sensor, and that is configured in a manner that the conductive parts electrically connect the electrode array of the substrate and the electrode array of the image sensor to each other via solder.

(11) A mobile camera that includes an image sensor module including:
  a substrate that includes an electrode array;
  an image sensor that includes an electrode array; and
  a connection device that includes a plurality of post parts including respective conductive parts and a base for supporting the plurality of post parts, that is interposed between the substrate and the image sensor, and that is configured in a manner that the conductive parts electrically connect the electrode array of the substrate and the electrode array of the image sensor to each other via solder.

(12) A method for producing an electronic component module, the method including:
  forming a connection device that includes a plurality of post parts including respective conductive parts and a base for supporting the plurality of post parts; and
  electrically connecting the electrode array of the substrate and the electrode array of the electronic component to each other via solder by using the conductive parts of the connection device.

(13) The method for producing an electronic component module according to (12), in which the formation of the connection device includes forming a conductive film on a base substance, and forming the conductive parts and the post parts including the conductive parts by removing a portion of the conductive film through cutting of the base substance on which the conductive film is formed.

(14) The method for producing an electronic component module according to (12), in which the formation of the connection device includes forming the base and main bodies of the post parts through injection molding in a manner that the main bodies protrude from a surface of the base, and forming the respective conductive parts on the formed main bodies.

REFERENCE SIGNS LIST 10 substrate
15 electrode array
20 image sensor
20 electrode array unit
30, 130, 230, 330 MID
30 MID
31a first surface
31b second surface
31 base
33, 133, 233, 333 post part
33a, 133a, 233a, 333a conductive part
33b, 133b, 233b, 333b through hole
33d, 233d, 333d protrusion part (main body)
33d1, 233d1, 333d1 substrate-side protrusion part (main body)
33d2, 133d2, 233d2, 333d2 component-side protrusion part (main body)
33c, 233c step part
100 image sensor module

What is claimed is:

1. An electronic component module, comprising:
a substrate that includes an electrode array;
an electronic component that includes an electrode array; and
a connection device that includes a plurality of post parts including respective conductive parts and a base for supporting the plurality of post parts, that is interposed between the substrate and the electronic component, and that is configured in a manner that the conductive parts electrically connect the electrode array of the substrate and the electrode array of the electronic component to each other via solder, wherein at least one of the post parts includes a first step part that is formed like a step from the base and that extends from a first surface side of the base, wherein a first protrusion part extends from the first step part, wherein the at least one of the post parts includes a second step part that is formed like a step from the base and that extends from a second surface side of the base, and wherein a second protrusion part extends from the second step part.

2. The electronic component module according to claim 1, wherein the connection device has a plurality of through holes in which the respective conductive parts are disposed.

3. The electronic component module according to claim 2, wherein axis centers of the through holes are disposed in a manner that the axis centers of the respective through holes are deviated from axis centers of the post parts.

4. The electronic component module according to claim 2, wherein axis centers of the respective through holes coincide with axis centers of the post parts.

5. The electronic component module according to claim 1, wherein
the base has a first surface that faces the substrate and a second surface that faces the electronic component, and
the post parts include main bodies that protrude from at least one of the first surface or the second surface.

6. The electronic component module according to claim 5, wherein a height of the main bodies from the first surface is different from a height of the main bodies from the second surface.

7. The electronic component module according to claim 1, wherein a main material of the base of the connection device is resin.

8. The electronic component module according to claim 7, wherein a Young's modulus of the main material of the connection device is smaller than a Young's modulus of the solder.

9. An endoscope that comprises an image sensor module including:
a substrate that includes an electrode array;
an image sensor that includes an electrode array; and
a connection device that includes a plurality of post parts including respective conductive parts and a base for supporting the plurality of post parts, that is interposed between the substrate and the image sensor, and that is configured in a manner that the conductive parts electrically connect the electrode array of the substrate and the electrode array of the image sensor to each other via solder, wherein at least one of the post parts includes a first step part that is formed like a step from the base and that extends from a first surface side of the base, wherein a first protrusion part extends from the first step part, wherein the at least one of the post parts includes a second step part that is formed like a step from the base and that extends from a second surface side of the base, and wherein a second protrusion part extends from the second step part.

10. A method for producing an electronic component module, the method comprising:
forming a connection device that includes a plurality of post parts including respective conductive parts and a base for supporting the plurality of post parts, wherein at least one of the post parts includes a first step part that is formed like a step from the base and that extends from a first surface side of the base, wherein a first protrusion part extends from the first step part, wherein the at least one of the post parts includes a second step part that is formed like a step from the base and that extends from a second surface side of the base, and wherein a second protrusion part extends from the second step part; and
electrically connecting an electrode array of a substrate and an electrode array of an electronic component to each other via solder by using the conductive parts of the connection device, wherein the forming the connection device includes:
forming a conductive film on a base substance; and
forming the conductive parts and the post parts including the conductive parts by removing a portion of the conductive film through cutting of the base substance on which the conductive film is formed.

11. A method for producing an electronic component module, the method comprising:

forming a connection device that includes a plurality of post parts including respective conductive parts and a base for supporting the plurality of post parts, wherein at least one of the post parts includes a first step part that is formed like a step from the base and that extends from a first surface side of the base, wherein a first protrusion part extends from the first step part, wherein the at least one of the post parts includes a second step part that is formed like a step from the base and that extends from a second surface side of the base, and wherein a second protrusion part extends from the second step part; and electrically connecting an electrode array of a substrate and an electrode array of an electronic component to each other via solder by using the conductive parts of the connection device, wherein the forming the connection device includes:

forming the base and main bodies of the post parts through injection molding in a manner that the main bodies protrude from a surface of the base; and forming the respective conductive parts on the formed main bodies.

12. The electronic component module according to claim 1, wherein the electronic component is an image sensor.

13. The method for producing an electronic component module according to claim 10, wherein the electronic component is an image sensor.

14. The method for producing an electronic component module according to claim 11, wherein the electronic component is an image sensor.

15. The electronic component module according to claim 1, wherein the first and second protrusion parts include portions of the base that are coated with a conductive film.

16. The electronic component module according to claim 15, wherein the base is formed from a resin material.

17. The electronic component module according to claim 1, wherein the at least one of the post parts is vertically symmetrical.

18. The endoscope according to claim 9, wherein the first and second protrusion parts include portions of the base that are coated with a conductive film.

19. The electronic component module according to claim 15, wherein the base is formed from a resin material.

20. The endoscope according to claim 9, wherein the at least one of the post parts is vertically symmetrical.

* * * * *